(12) United States Patent
Vela Hernández et al.

(10) Patent No.: US 9,789,115 B2
(45) Date of Patent: Oct. 17, 2017

(54) USE OF SIGMA LIGANDS IN OPIOID-INDUCED HYPERALGESIA

(75) Inventors: José Miguel Vela Hernández, Barcelona (ES); Daniel Zamanillo-Castanedo, Barcelona (ES); Margarita Puig Riera de Conias, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/814,148

(22) PCT Filed: Aug. 2, 2011

(86) PCT No.: PCT/EP2011/063286
§ 371 (c)(1),
(2), (4) Date: Mar. 7, 2013

(87) PCT Pub. No.: WO2012/016980
PCT Pub. Date: Feb. 9, 2012

(65) Prior Publication Data
US 2013/0158033 A1   Jun. 20, 2013

(30) Foreign Application Priority Data

Aug. 3, 2010  (EP) .................................... 10382215

(51) Int. Cl.
*A61K 31/5377* (2006.01)
*A61K 31/415* (2006.01)
*A61K 31/4155* (2006.01)

(52) U.S. Cl.
CPC ........ *A61K 31/5377* (2013.01); *A61K 31/415* (2013.01); *A61K 31/4155* (2013.01)

(58) Field of Classification Search
None
See application file for complete search history.

(56) References Cited

U.S. PATENT DOCUMENTS

| 2,908,677 A | 10/1959 | Straley et al. |
| 3,514,439 A | 5/1970 | Wehrli et al. |
| 3,980,675 A | 9/1976 | Venturella et al. |
| 4,024,175 A | 5/1977 | Satzinger et al. |
| 4,207,392 A | 6/1980 | Shiao et al. |
| 4,234,479 A | 11/1980 | Mennicke et al. |
| 4,234,616 A | 11/1980 | Shu et al. |

(Continued)

FOREIGN PATENT DOCUMENTS

| EP | 0248594 A2 | 12/1987 |
| EP | 0414289 A1 | 2/1991 |

(Continued)

OTHER PUBLICATIONS

Kenakin, A Pharmacology Primer, The Evolving Pharmacology of GPCR's, 2006, pp. 27-60.*

(Continued)

*Primary Examiner* — Kathrien Cruz
*Assistant Examiner* — Andrew Lee
(74) *Attorney, Agent, or Firm* — Jenkins, Wilson, Taylor & Hunt, P.A.

(57) ABSTRACT

The invention refers to the use of a sigma ligand, particularly a sigma ligand of formula (I) to prevent and/or treat opioid-induced hyperalgesia (OIH) associated to opioid therapy.

6 Claims, 11 Drawing Sheets

PARADIGM 2:

(56) References Cited

U.S. PATENT DOCUMENTS

| | | | |
|---|---|---|---|
| 4,337,263 A | 6/1982 | Techer et al. |
| 5,948,777 A | 9/1999 | Bender et al. |
| 6,057,371 A | 5/2000 | Glennon |
| 6,100,259 A | 8/2000 | Xiang et al. |
| 6,166,072 A | 12/2000 | Bell et al. |
| 6,492,529 B1 | 12/2002 | Kapadia et al. |
| 6,509,367 B1 | 1/2003 | Martin et al. |
| 7,091,257 B2 | 8/2006 | Greer, IV |
| 7,105,646 B2 | 9/2006 | Chamberlain et al. |
| 7,696,199 B2 | 4/2010 | Laggner et al. |
| 7,799,782 B2 | 9/2010 | Munson et al. |
| 7,988,966 B2 | 8/2011 | Pavone et al. |
| 8,193,223 B2 | 6/2012 | Jagerovic et al. |
| 8,293,740 B2 | 10/2012 | Laggner et al. |
| 8,314,096 B2 | 11/2012 | Laggner et al. |
| 8,470,867 B2 | 6/2013 | Laggner et al. |
| 8,492,425 B2 | 7/2013 | Torrens Jover et al. |
| 8,877,753 B2 | 11/2014 | Buschmann et al. |
| 2001/0036951 A1 | 11/2001 | Farrar et al. |
| 2003/0144309 A1 | 7/2003 | Choon-Moon |
| 2005/0020483 A1 | 1/2005 | Oksenberg et al. |
| 2006/0106068 A1 | 5/2006 | Laggner |
| 2007/0208134 A1 | 9/2007 | Hunter et al. |
| 2008/0058362 A1 | 3/2008 | Singh et al. |
| 2008/0125416 A1 | 5/2008 | Laggner et al. |
| 2008/0161604 A1 | 7/2008 | Calvani et al. |
| 2009/0018151 A1 | 1/2009 | Fink |
| 2009/0264442 A1 | 10/2009 | Cuberes-Altisent et al. |
| 2009/0325975 A1 | 12/2009 | Buschmann |
| 2010/0081659 A1 | 4/2010 | Laggner |
| 2010/0190078 A1 | 7/2010 | Rapaport et al. |
| 2010/0190780 A1 | 7/2010 | Laggner et al. |
| 2010/0190781 A1 | 7/2010 | Laggner et al. |
| 2010/0240711 A1 | 9/2010 | Takada et al. |
| 2011/0112095 A1 | 5/2011 | Buschmann et al. |
| 2011/0269727 A1 | 11/2011 | Toledano |
| 2012/0141606 A1 | 6/2012 | Baeyens-Cabrera et al. |
| 2012/0232093 A1 | 9/2012 | Cuberes-Altisent et al. |
| 2012/0283262 A1 | 11/2012 | Soler Ranzani et al. |
| 2012/0302568 A1 | 11/2012 | Vela Hernandez et al. |
| 2012/0316336 A1 | 12/2012 | Berenguer Maimo et al. |
| 2013/0109692 A1 | 5/2013 | Vela Hernandez et al. |
| 2013/0143884 A1 | 6/2013 | Cuberes-Altisent et al. |
| 2013/0158033 A1 | 6/2013 | Vela Hernandez et al. |
| 2013/0324535 A1 | 12/2013 | Zamanillo-Castanedo et al. |
| 2015/0018354 A1 | 1/2015 | Buschmann et al. |
| 2016/0220575 A1 | 8/2016 | Baeyens-Cabrera et al. |

FOREIGN PATENT DOCUMENTS

| | | | |
|---|---|---|---|
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 B1 | 5/1994 |
| EP | 0975648 A1 | 2/2000 |
| EP | 1130018 A1 | 9/2001 |
| EP | 1634872 A1 | 3/2006 |
| EP | 1634873 A1 | 3/2006 |
| EP | 1787679 A1 | 5/2007 |
| EP | 1829866 A1 | 9/2007 |
| EP | 1829875 A1 | 9/2007 |
| EP | 1847542 A1 | 10/2007 |
| EP | 2090311 A1 | 8/2009 |
| EP | 2112139 A1 | 10/2009 |
| EP | 2 113 501 A1 | 11/2009 |
| EP | 2 116 539 A1 | 11/2009 |
| EP | 2254579 A1 | 12/2010 |
| EP | 2292236 A1 | 3/2011 |
| EP | 2335688 A1 | 6/2011 |
| EP | 2353591 A1 | 8/2011 |
| EP | 2353598 A1 | 8/2011 |
| EP | 2361904 A1 | 8/2011 |
| EP | 2395003 A1 | 12/2011 |
| EP | 2415471 A1 | 2/2012 |
| EP | 2426111 A1 | 3/2012 |
| EP | 2426112 A1 | 3/2012 |
| EP | 2460519 A1 | 6/2012 |
| EP | 2460804 A1 | 6/2012 |
| EP | 2524694 A1 | 11/2012 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 | 10/1967 |
| GB | 1496411 A | 12/1977 |
| GB | 2026482 A | 2/1980 |
| IL | 151533 B | 3/2008 |
| JP | 1992364129 A | 12/1992 |
| JP | 10036259 A | 2/1998 |
| JP | 10055048 A | 2/1998 |
| JP | 2004196678 A | 7/2004 |
| JP | 2008/510767 A | 4/2008 |
| JP | 2008179541 A | 8/2008 |
| RU | 2218187 C2 | 10/2003 |
| RU | 2322977 C1 | 4/2008 |
| RU | 2 382 646 C1 | 2/2010 |
| SU | 11248 A1 | 9/1929 |
| WO | WO-91/09594 A1 | 7/1991 |
| WO | WO-92/09560 A1 | 6/1992 |
| WO | WO-93/23383 A1 | 12/1992 |
| WO | WO-1996/016063 A1 | 5/1996 |
| WO | WO-1998/046618 A1 | 10/1998 |
| WO | WO-99/01444 A1 | 1/1999 |
| WO | WO-99/21824 A1 | 5/1999 |
| WO | WO-99/31057 A1 | 6/1999 |
| WO | WO-99/31074 A2 | 6/1999 |
| WO | WO-99/31075 A1 | 6/1999 |
| WO | WO-1999059409 A1 | 11/1999 |
| WO | WO-99/61424 A1 | 12/1999 |
| WO | WO-00/31020 A1 | 2/2000 |
| WO | WO-0020005 A1 | 4/2000 |
| WO | WO-0027394 A1 | 5/2000 |
| WO | WO-0040275 A2 | 7/2000 |
| WO | WO-0073259 A1 | 12/2000 |
| WO | WO-0073296 A2 | 12/2000 |
| WO | WO-0073300 A1 | 12/2000 |
| WO | WO-02085839 A1 | 10/2002 |
| WO | WO-02092573 A2 | 11/2002 |
| WO | WO-02102387 A1 | 12/2002 |
| WO | WO-2003080183 A1 | 10/2003 |
| WO | WO-2004016592 A1 | 2/2004 |
| WO | WO 2004017961 A2 | 3/2004 |
| WO | WO-2004046129 A2 | 6/2004 |
| WO | WO-2005061462 A2 | 7/2005 |
| WO | WO-2006010587 A1 | 2/2006 |
| WO | WO-2006-021462 A1 | 3/2006 |
| WO | WO-2006021463 A1 | 3/2006 |
| WO | WO-2006027221 A1 | 3/2006 |
| WO | WO-2006118307 A1 | 11/2006 |
| WO | WO-07002559 A1 | 1/2007 |
| WO | WO-2007025613 A2 | 3/2007 |
| WO | WO-2007046550 A1 | 4/2007 |
| WO | WO-2007046650 A1 | 4/2007 |
| WO | WO-07079086 A1 | 7/2007 |
| WO | WO-2007090661 A2 | 8/2007 |
| WO | WO-2007-098953 A1 | 9/2007 |
| WO | WO 2007/098963 | 9/2007 |
| WO | WO-2007098939 A1 | 9/2007 |
| WO | WO-2007098964 A2 | 9/2007 |
| WO | WO-2007108517 A1 | 9/2007 |
| WO | WO-2007110221 A1 | 10/2007 |
| WO | WO-2007141018 A1 | 12/2007 |
| WO | WO-2008015266 A1 | 2/2008 |
| WO | WO-2008055932 A1 | 5/2008 |
| WO | WO-2008108517 A2 | 9/2008 |
| WO | WO-2008149062 A1 | 12/2008 |
| WO | WO-2009038112 A1 | 3/2009 |
| WO | WO-2009071657 A1 | 6/2009 |
| WO | WO-2009103487 A1 | 8/2009 |
| WO | WO 2009/130310 | 10/2009 |

(56) References Cited

FOREIGN PATENT DOCUMENTS

| | | |
|---|---|---|
| WO | WO-2009130314 A1 | 10/2009 |
| WO | WO-2009130331 A1 | 10/2009 |
| WO | WO-2011095579 A1 | 1/2011 |
| WO | WO-2011018487 A1 | 2/2011 |
| WO | WO-2011064296 A1 | 6/2011 |
| WO | WO-2011064315 A1 | 6/2011 |
| WO | WO-2011095584 A1 | 8/2011 |
| WO | WO-2011095585 A1 | 8/2011 |
| WO | WO-2011144721 A1 | 11/2011 |
| WO | WO-2011147910 A1 | 12/2011 |
| WO | WO-2012016980 A1 | 2/2012 |
| WO | WO-2012019984 A1 | 2/2012 |
| WO | WO-2012072781 A1 | 6/2012 |
| WO | WO-2012072782 A1 | 6/2012 |
| WO | WO-2012/156497 A1 | 11/2012 |
| WO | WO-2012/158413 A1 | 11/2012 |
| WO | WO-2014170319 A1 | 10/2014 |
| WO | WO-2014207024 A1 | 12/2014 |
| WO | WO-2015036470 A1 | 3/2015 |
| WO | WO-2015091505 A1 | 6/2015 |
| WO | WO-2015091508 A1 | 6/2015 |

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

Bryant et al., Opioids and addiction: Emerging pharmaceutical strategies for reducing reward and opponent processes, Clinical Neuroscience Research, 2005, 5, pp. 103-115.*

International Search Report issued on Jan. 31, 2012 in priority International Patent Application No. PCT/EP2011/063286.

Chien, Chih-Chen, et al., "Sigma antagonist potentiate opioid analgesia in rats," Neuroscience Letters, 190 (1995), pp. 137-139.

Anonymous "Opioid-Induced hyperalgesia," http://web.archive.org/web/20080712205531/http://en.wikipedia.org/wiki/Opioid-induced_hyperalgesia (retrieved Oct. 1, 2010.

Lee, M. et al., "A Comprehensive Review of Opioid-Induced Hyperalgesia," Pain Physician. vol. 14 pp. 145-161 (2011).

Angst, M.S. and Clark, J.D., "Opioid-induced Hyperalgesia: A Qualitative Systematic Review," Anesthesiology. vol. 104 pp. 570-587 (2006).

Brennan et al., "Characterization of a rat model of incisional pain," Pain. vol. 64 pp. 493-501 (1996).

Celerier et al., "Progressive Enhancement of Delayed Hyperalgesia Induced by Repeated Heroin Administration: A Sensitization Process," The Journal of Neuroscience. vol. 21, No. 11 pp. 4074-4080 (2001).

Chien, C.C. and Pasternak, G.W., "Sigma antagonists potentiate opioid analgesia in rats," Neuroscience Letters. vol. 190 pp. 137-139 (1995).

Guignard et al., "Acute Opioid Tolerance: Intraoperative Remifentanil Increases Postoperative Pain and Morphine Requirement," Anesthesiology. vol. 93 pp. 409-417 (2000).

Hellewell, S.B. and Bowen, W.D., "A sigma-like binding site in rat pheochromocytoma (PC12) cells: decreased affinity for (+)-benzomorphans and lower molecular weight suggest a different sigma receptor form from that of guinea pig brain," Brain Research. vol. 527.

Leitner et al., "Regional variation in the ratio of $\sigma$-1 to $\sigma$2 binding in rat brain," European Journal of Pharmacology. vol. 259 pp. 65-69 (1994).

Mao,J., "Opioid-induced abnormal pain sensitivity: implications in clinical opioid therapy," Pain. vol. 100 pp. 213-217 (2002).

Mei and Pasternak, "$\sigma$1 Receptor Modulation of Opioid Analgesia in the Mouse," The Journal of Pharmacology and Experimental Therapeutics. vol. 300, No. 4 pp. 1070-1074 (2002).

Merskey, IASP, Class. Chronic Pain, 2nd Edition; IASP Press; p. 210-213 (2002).

Prasad et al., "Exon-Intron Structure, Analysis of Promoter Region, and Chromosomal Localization of the Human Type 1 $\sigma$ Receptor Gene," Journal of Neurochemistry. vol. 70 pp. 443-451 (1998).

Quirion et al., "A proposal for the classification of sigma binding sites," Trends Pharmacol. Sci. vol. 13 pp. 85-86 (1992).

Ronsisvalle et al., "Opioid and sigma receptor studies. New development in the design of selective sigma ligands," Pure Appl. Chem. vol. 73, No. 9 pp. 1499-1509 (2001).

Silverman, M., "Opioid Induced Hyperalgesia: Clinical Implications for the Pain Practitioner," Pain Physician. vol. 12 pp. 679-684 (2009).

Smith M.T., "Opioid-induced hyperalgesia, opioid rotation and opioid combinations," Acute Pain. vol. 10 pp. 199-200 (2008) [Abstract].

Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).

Hiranita et al., "Reinforcing effects of sigma-receptor agonists in rats trained to self-administer cocaine," J Pharmacol Exp Ther. Feb. 2010;332(2):515-524. (2010).

Office Action and Search Report corresponding to Taiwanese Patent Application (Translation) [undated].

Wang, Chinese Journal of Medicine (2008).

Lytle et al. "Effects of long-term corn consumption on brain serotonin and the response to electric shock", Science vol. 190 pp. 692-694 (1975).

"Chemotherapy at home, pain and its treatment", Soins, Office De Publicite Generale, Paris, FR, (Sep. 1, 1989), No. 528, ISSN 0038-0814, pp. 17-20, XP009107313 [A] 1-16. * p. 19 *.

Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.

Abbott, C, A., et al., "The North-West Diabetes Foot Care Study: incidence of, and risk factors for, new diabetic foot ulceration in a community-based patient cohort", Diabetic Medicine, vol. 19, 2002, pp. 377-384.

Abraham, D.J., et al., "Burger's Medicinal Chemistry: Drug Discovery and Development" 7th edition, 8 vol. set, 2010.

Abrams, P., et al., "The standardisation of terminology of lower urinary tract function: report from the standardisation sub-committee of the International Continence Society", Neurology andUrodynamics, 21, 2002, pp. 167-178.

Acta Obstetrica Gynecologica Japonica, 2000, vol. 52 (6), pp. 117-120.

Advokat, C., et al., "Selective antinociceptive effect of excitatory amino acid antagonists in intact and acute spinal rats," Pharmacology Biochemistry and Behavior 51(4):855-60 1995.

Alberts, D.S., et al., "Cisplatin-associated neurotoxicity: can it be prevented?" Anti-cancer Drugs, 1995, vol. 6, pp. 369-383.

Almerico, AM., "1-Methyi-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.

Anderson, B. D. et al., "Preparation of Water-Soluble Compounds Through Salt Formation" The Practice of Medicinal Chemistry, Chapter 34, pp. 739-754 (1996).

Anton, E., "Delayed toxicity of cyclophosphamide on the bladder of DBA/2 and C57BL/6 female mouse," Int. J. Exp. Path., 83, 2002, pp. 47-53.

Arafa, et. al., Journal of Medicinal Chemistry, 2005, American Chemical Society, vol. 48, pp. 5480-5488.

Arthritis [online], [retrieved on Nov. 20, 2007]. Retrieved from the Internet, URL; http://www.nlm.nih.gov/medlineplus/ency/article/001243.htm>.

Asano, T., et al. Antinociception by epidural and systemic alpha(2)adrenoceptor agonists and their binding affinity in rat spinal cord and brain, *Anesth Anal g.* 2000; 90 (2): 400-407.

(56) References Cited

OTHER PUBLICATIONS

Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-Isoxazolecarboxylates as Starting Materials for a Convenient Route to 3(2H) Furanones and 3(2H) Iminofuranes", Tetrahedron Lett., 25(38), pp. 4313-4316; 1984.
Batson, et al., "a-Hydroxy Cyclopentenones from a-Diketones", Organic Letters, vol. 7, No. 13, pp. 2771-2774, 2005.
Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.
Bennett, G. J. "Pathophysiology and Animal Models of Cancer-Related Painful Peripheral Neuropathy", The Oncologist, 2010, 15 (suppl2), pp. 9-12.
Berge, S.M. et al., "Pharmaceutical Salts," Journal of Pharmaceutical Sciences, 1977, vol. 66, No. 1, pp. 1-19.
Bon, K., et al., "Characterization of cyclophosphamide cystitis, a model of visceral and referred pain, in the mouse: species and strain differences.", J Urol., (2003), vol. 170, No. 3, pp. 1008-1012.
Botting, R.M.; Clinical Infectious Diseases, 2000, 31, S202-10.
Boulton, A.J.M., et al., "Diabetic Neuropathies" Diabetes Care, vol. 28, No. 4, Apr. 2005, pp. 956-962.
Bowen W. D., Pharmaceutica *Acta Helvetiae*; 2000; 74:211-218.
Brussee, et al., Diabetes, 2008, 57: 1664-1673, "Distal Degenerative Sensory Neuropathy in a Long-Term Type 2 Diabetes Rat Model".
Bryans, J.S., et al., "3-substituted GABA analogs with central nervous system activity: a review," Med Res Rev, 19, 1999, pp. 149-177.
Bryans, J.S., et al., "Identification of novel ligands for the gabapentin binding site on the alpha-2-delta subunit of a calcium channel and their evaluation as anticonvulsant agents", J. Med. Chern. 41, 1998, pp. 1838-1845.
Buerkle, H., Yaksh, T. L. Pharmacological evidence for different alpha 2-adrenergic receptor sites mediating analgesia and sedation in the rat, *Br J Anaesth*. 1998; 81 (2): 208-215.
Bura, S.A. et al., "Evaluation of the Effect of the Selective Sigma-1 Receptor Antagonist SIRA in Neuropathic Pain Using an Operant Model", Eur J. Pain Supplements 2010, vol. 4, p. 49 (Abstract Only).
Buvanendran, A., et al. "Characterization of a New Animal Model for Evaluation of Persistent Postthoracotomy Pain", Anesth Analg, 2004, vol. 99, pp. 1453-1460.
Cancer [online], [retrieved on Jul. 6, 2007]. Retrieved from the Internet, URL; http://www.nim.nih.gov /medlineplus/cancer.html>.
Lala et al., Cancer and Metastasis Reviews, 17(1), 91-106, 1998.
Cao, J., et al., "Dual Probes for the Dopamine Transporter and sigmal Receptors: Novel Piperazinyl Alkyl-bis(4-fluorophenyl)amine Analogues as Potential Cocaine-Abuse Therapeutic Agents", J. Med. Chem, 2003, pp. 2589-2598.
Carlsson, et al., "Interaction of pentobarbital and morphine in the tail-flick test performed on rates: synergism at the spinal and antagonism at the supraspinal level", NeuroSci. Lett.; 1986; 71; pp. 356-360.
Carrie, et al., Int Orthopaedics vol. 30, pase 445-451. publication year: 2006.
Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans—Smart Nurse, Nov. 2007, vol. 9, No. II, pp. 1238-1239.
Cepeda, MS, "Comparison of Morphine, ketorolac, and their combination for postoperative pain: results form a large, randomized, double-blind trial", anesthesiology, 2005, vol. I03, No. 6, pp. 1225-1232.
Cersosimo, R.J., "Oxaliplatin-Associated Neuropathy: A Review", The Annals of Pharmacotherapy, 2005 vol. 39 pp. 128-135.

Chaplan S. R., et al., "Quantitative assessment of tactile allodynia in the rat paw", J. Neurosci. Methods, (1994), vol. 53, pp. 55-63.
Chaudhry, V., et al., "Bortezomib and thalidomide-induced subacute demyelinating polyneuropathy," Clinical Neurophysiology, 2009, vol. 120, p. ell.
Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.
Cheng, et al., Modern Bone Science, Modern Orthopaedics, "14.2.2 Drug Analgesia," p. 164, 2010, including English translation.
Chen, S.R., et al., "Synergistic Effect between Intrathecal Non-NMDA Antagonist and Gabapentin on Allodynia Induced by Spinal Nerve Ligation in Rats", Anesthesiology, 2000, vol. 92, pp. 500-506.
Chen, D., et al., "Development and application of rodent models for type 2 Diabetes", Diabetes, Obesity and Metabolism, vol. 7, 2005, pp. 307-317.
Cherny, N., "Opioids and the Management of Cancer Pain", Eur. J. Cancer Supplement 2005, vol. 3, pp. 61-75.
Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61. (with English abstract).
Chien, et al., "Selective Antagonism of Opioid Analgesia by a Sigma System," J. Pharmacol. Exp. Ther.; 1994; 271; pp. 1583-1590.
STN serach abstract JP10055048.
Clark, J.B., et al., "The Diabetic Zucker Fatty Rat (41611)", Proceedings of the society for experimental Biology and Medicine, 1983, vol. 173, pp. 68-75.
Cobos, E. J., et al., Pharmacology and therapeutic potential of Sigma(1) receptor ligands. *Curr. Neuropharmacol.* 2008; 6, 344-366.
Consilium MedSigma-receptors: new potentials of the treatment of depressions. Consilium Medicumicum 2012, vol. 14, No. 2 (found in the Internet: URL<new.Consiliummedicum.com/magazines/cm/medicum/article/21505, paragraphs 4-8).
Final Office Action dated Nov. 29, 2007 in related priority U.S. Appl. No. 10/978,250.
Final Office Action dated Oct. 20, 2008 in related priority U.S. Appl. No. 10/978,250.
Non-Final Office Action dated Apr. 16, 2008 in related priority U.S. Appl. No. 10/978,250.
Non-Final Office Action dated Jun. 14, 2007 in related priority U.S. Appl. No. 10/978,250.
Requirement for Restriction/Election dated Apr. 5, 2007 in related priority U.S. Appl. No. 10/978,250.
Coxon, et al., "Acid-catalysed Rearrangements of trans- and cis-1-Acetoxy-3,4-epoxypentane and 1-Acetoxy-4,5-epoxyhexane", J. Chem. Soc. Chem. Commun., 8, pp. 261-262, 1973.
D'Amour, F. E. and Smith, D. L. A method for determining the loss of pain sensation, *J. Pharmacal. Exp. Ther.* 1941; 72:74-79.
Dani, et al. (2007) The local antinociceptive effects of paracetamol in neuropathic pain are mediated by cannabinoid receptors. European Journal of Pharmacology 573(1-3): 214-215.
Daousi, C., et al., "Chronic painful peripheral neuropathy in an urban community: a controlled comparison of people with and without diabetes", Diabetic Medicine, vol. 21, 2004, pp. 976-982.
Dapeng Li "The Role of Glial Cells in . . . Pain", Thesis of Huazhong, University of Science and Technology, 2006, p. 24; Publication Date: Feb. 19, 2008.
Database WPI Week 200451 Thomson Scientific, London, GB; An 2004-529624-& JP 2004 196678 A (Dainippon Pharm Co Ltd) Jul. 15, 2004 (Jul. 15, 2004).
Dauben, W., et al., "Organic Reactions at High Pressure Preparation of Wittig Phosphonium Salts at Ambient Temperature", J. Org. Chern., 1984, vol. 49, pp. 4293-4295.
Davies, A., et al., "Functional biology of the alpha-2-delta subunits of voltage-gated calcium channels," trends in Pharmacological Sciences, vol. 28, No. 5, 2007, pp. 220-228.
DeHaven-Hudkins, et al., "Characterization of the binding of [H](+)-pentazocine to σ recognition sites in guinea pig brain,"

(56) References Cited

OTHER PUBLICATIONS

European Journal of Pharmacology—Molecular Pharmacology Section, 1992, vol. 227, pp. 371-378.
Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9. * the whole document *.
Dewar, M. J. S., "Attempts to find new Antimalarials. Part XXI", Journal of the Chemical Society, (1944), pp. 615-619.
Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.
Diaz, J.L. et al., "Selective Sigma-1 Receptor Antagonists: Emerging Target for the Treatment of Neuropathic Pain", Cent. Nerv. Syst. Agents in Med. Chem. 2009, vol. 9 pp. 172-183.
Diaz, J.L., et al., "Synthesis and Biological Evaluation of the 1-Arylpyrazole Class of sigma 1 Receptor Antagonists: Identification of 4-{2-[5-Methyl-1-(naphthalen-2-yl)-1 H-pyrazol-3-yloxy]ethyl}morpholine (S1RA, E-52862)", Journal of Medicinal Chemistry, (Oct. 11, 2012), vol. 55, No. 19, doi:10.1021/jm3007323, ISSN 0022-2623, pp. 8211-8224, XP055094581 [Y] 1-14,16 * abstract ** p. 8219, column left, paragraphs 3-4 *.
Dixon, W. J., "Efficient analysis of experimental observations", Ann. Rev. Pharmacal. Toxicol., 20,1980, pp. 441-462.
Dmitrieva, N., et al., "The role of nerve growth factor in a model of visceral inflammation", Neuroscience, vol. 78, No. 2, 1997, pp. 449-459.
Dosen-Micovic, et. al., Bioorganic and Medicinal Chemistry, 2006, Elsevier, vol. 14, pp. 2887-2895.
Dougherty, P.M., et al. "Taxol-induced sensory disturbance is characterized by preferential impairment of myelinated fiber function in cancer patients", Pain, 2004, vol. 109, pp. 132-142.
Drug encyclopedia M., RLS 2001, pp. 572-573, articles "Morphine", "Morphine Sulfate".
Du, J., et al. "Kainate-induced Excitation and Sensitization of Nociceptors in Normal and Inflamed Rat Glabrous Skin", Neuroscience, 2006, vol. 137, pp. 999-1013.
Dugowson, et al.; Phys. Med. Rehabil. Clin. N. Am. 2006, 17, 347-354.
Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.
Dunlap, B., et al., "Chemotherapy-Induced Peripheral Neuropathy Measurement", The Journal of Supportive Oncology, 2006, vol. 4, 8, pp.
Dworkin R.H., "An Overview of Neuropathic Pain: Syndromes, Symptoms, Signs, and Several Mechanisms," The Clinical Journal of Pain 2002, vol. 18, pp. 343-349.
Dworkin, R.H. et a., "Recommendations for Ihe Pharmacological Management of Neuropathic Pain: Literature Update", Mayo Clin. Proc., 2010, 85(3)(Suppl), S3-S14.
Effenberger, F., et al., Chern. Ber., 102(10), 3260-3267, 1969.
Eghbaldar, et al., "Substances aromatisantes separation chirale par chromatographie gazeuse" Parfums, Cosmetiques, Aromes, 104, pp. 71-78, 1992.
Eisenach, J. C., et al., Intrathecal, but not intravenous, clonidine reduces experimental thermal or capsaicin-induced pain and hyperalgesia in normal volunteers; *Anesth Analg*; 1998; 87: 591-596.
Entrena, J.M., et al., "Sigma-I receptors are essential for capsaicin-induced mechanical hypersensitivity: Studies with selective sigma-1 ligands and sigma-1 knockout mice", Pain, (2009), vol. 143, pp. 252-261.
Epilepsy [online], [retrieved on Nov. 20, 2007]. Retrieved from the Internet, URL; http://www .nim.nih.gov /medlineplus/ ency/ article/ 000694.htm>.

Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.
Epstein, et al., "Oral topical doxepin rinse: analgesic effect in patients with oral mucosal pain due to cancer or cancer therapy" (2001) Oral Oncology, 37:632-637.
European Patent Office, European Search Report for EP 04077421. 8, dated Feb. 1, 2005.
European Search Report dated Apr. 19, 2010 in connection with priority European Application No. EP10382024.7.
European Search Report dated Dec. 20, 2013 in connection with priority European Application No. EP13382246.0.
European Search Report dated Feb. 5, 2010 in connection with Application No. EP09382144.
European Search Report dated Jan. 31, 2011 in connection with priority European Patent Application No. 10382326.6.
European Search Report dated Jul. 1, 2010 in connection with priority European Patent Application No. EP10382025.
European Search Report dated Jun. 16, 2010 in connection with Application No. EP 10382023.
European Search Report dated Mar. 11, 2011 in connection with priority European Application No. EP10382330.8.
European Search Report dated Apr. 14, 2010 in connection with Application No. EP09382261.
European Search Report dated May 3, 2013 in connection with priority European Patent Application No. EP13382140.
European Search Report dated Oct. 1, 2010 in connection with Application No. EP10382215.1.
European Search Report dated Oct. 18, 2011 in connection with priority European Application No. EP11382157.3.
European Search Report dated Oct. 2, 2008 in connection with Application No. EP 08380122.
European Search Report dated Oct. 29, 2010 in connection with priority European Application No. EP10382136.
European Search Report dated Sep. 12, 2008 in connection with Application No. EP08384006.
European Search report dated Oct. 22, 2010 by European Patent Office in connection with European Application No. EP 10 38 2148.
Falk et al. "Pain and Nociception: Mechanisms of Cancer-Induced Bone Pain", Journal Clinical Oncology, 2014, vol. 32, pp. 1647-1654.
Field, M.J., et al., "Identification of the alpha-2-delta-1 subunit of voltage-dependent calcium channels as a molecular target for pain mediating the analgesic actions of pregabalin", PNAS, vol. 103, No. 46, Nov. 14, 2006, pp. 17537-17542.
Finnerup, N.B., et al. "The evidence for pharmacological treatment of neuropathic pain", Pain, 2010, vol. 150, pp. 573-581.
Forsyth, P.A., et al., "Prospective study of paclitaxel-induced peripheral neuropathy with quantitative sensory testing", Journal of Neuro-Oncology, 1997, vol. 35, pp. 47-53.
Friedman, J.E., et al., Altered expression of muscle glucose transporter GLUT-4 in diabetic fatty Zucker rats (ZDF/Drtfa), American Physiological Society, 1991, E782-E788.
Gabriel, A.F., Preoperative housing in an enriched environment significantly reduces the duration of post-operative pain in a rat model of knee inflammation, Neurosci. Lett. 2010, vol. 469, No. 2, pp. 219-232.
Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 f pp. 732-734.
Gentili, M., et al., Intra-articular morphine and clonidine produce comparable analgesia but the combination is not more effective, *Br J Anaesth*. 1997; 79 (5): 660-661.
Glass et al., "Evaluation of pentamorphone in humans: a new potent opiate," Anesth. Analg. Mar. 1989, 68(3) 302-7.
Goblirsch, M.J., et al., "Biology of Bone Cancer Pain," Clin. Cancer Res. 2006 vol. 12 (20 Suppl.), pp. 6231s-6235s.
Goodman, et al., "The Pharmacological Basis of Therapeutics", 8th Ed.; 13-18. , 1992.

(56) References Cited

OTHER PUBLICATIONS

Gordois, A., et al., "The Health Care Costs of Diabetic Peripheral Neuropathy in the U.S.", Diabetes Care, vol. 26, No. 6, Jun. 2003, pp. 1790-1795.

Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.

Grahame-Smith, D.G., et al., Oxford textbook on clinical pharmacology and drug therapy M., "Meditsina", 2000, pp. 658-661, Chapter "Narcotic analgesics".

Grover, S., et al., "Role of inflammation in bladder function and interstitial cystitis", Therapeutic Advances in Urology, 3(1 ), 2011, pp. 19-33.

Haleblian, "Characterization of Habits and Crystalline Modification of Solids and Their Pharmaceutical Applications," Journal of Pharmaceutical Sciences, vol. 64, No. 8 pp. 1269-1288 (1975).

Hall, J. J E.,Uhrich, T. D., Ebert, T. J. Sedative, analgesic and cognitive effects of clonidine infusions. In humans, *Br J Anaesth.* 2001; 86 (1): 5-11.

Hammack, et al., "Phase III evaluation of nortriptyline for alleviation of symptoms of cis-platinum-induced peripheral neuropathy" (2002) Pain, 98:195-203.

Hancock, et al., "Characteristics and Significance of the Amorphous State in Phamnaceutical Systems," Journal of Phamnaceutical Sciences, vol. 86, No. 1 pp. 1-12 (1997).

Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.

Harden, N., et al., "Unmet Needs in the Management of Neuropathic Pain", Journal of Pain and Symptom Management, 2003, 25, 5S, S12-S17.

Hartwig, J., "Synthesis, Structure, and Reactivity of a Palladium Hydrazonato Complex: A New Type of Reductive Elimination Reaction to FormC—N Bonds and Catalytic Arylation of Benzophenone Hydrazone", Angew. Chern. Int. Ed., 1998, vol. 37, No. 15, pp. 2090-2093.

Hellewell, S.B., et al., "A sigma-likebinding site in rat pheochromocytoma (PC12) cells: decreased affinity for (+)-benzomorphans and lower molecular weight suggest a different sigma receptor form from that of guinea pig brain," Brain Research, vol. 527, pp. 244-253.

Herndon, et al.; Pharmacotherapy, 2008, 28(6), 788-805.

Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).

Hileman, G.A., et al., "Response surface optimization of high dose pellets by extrusion and spheronization," International Journal of Pharmaceutics, 1993, vol. 100, pp. 71-79.

Hinz et al., FASEB Journal, 2007, 7, 2343-2351.

Narujo, Hiroyuki et al., Cancer Pain Treatment—Clinical Oral Morphine Extended-Release Tablets (once/day), 5th, Pharma Medical, 2007, including English language translation.

Horner, et al., "Azo-aryle und Phenazine aus primaren Arylaminanionen durch Autoxydation", Chern. Ber., 96, pp. 786-793, 1963.

Hsu, et al., Toxic. Appl. Pharmac., vol. 73, No. 3, p. 411-415, 1984.

IASP Classification of Chronic Pain, 2002, 2nd edition, pp. 201-213.

International Preliminary Report of Patentability with Written Opinion of the International Searching Authority dated Nov. 27, 2012 in connection with International Application No. PCT/EP2011/058633.

International Preliminary Report of Patentability with Written Opinion of the International Searching Authority dated Feb. 14, 2012 in connection with International Application No. PCT/EP2010/061720.

International Preliminary Report of Patentability with Written Opinion of the International Searching Authority dated May 30, 2012 in connection with International Application No. PCT/EP2010/068213.

International Preliminary Report of Patentability with Written Opinion of the International Searching Authority dated Feb. 12, 2013 in connection with International Patent Application No. PCT/EP2011/063583.

International Preliminary Report of Patentability with Written Opinion of the International Searching Authority dated Aug. 7, 2012 in connection with International Application No. PCT/EP2011/051644.

International Preliminary Report of Patentability with Written Opinion of the International Searching Authority dated Aug. 7, 2012 in connection with International Application No. PCT/EP11/51643.

International Preliminary Report of Patentability with Written Opinion of the International Searching Authority dated Aug. 24, 2010 in connection with International Application No. PCT/EP2009/001109.

International Preliminary Report of Patentability with Written Opinion of the International Searching Authority dated Dec. 29, 2015 in connection with International Application No. PCT/EP2014/063360.

International Preliminary Report of Patentability with Written Opinion of the International Searching Authority dated Feb. 28, 2007 in connection with International Application No. PCT/EP2005/009375.

International Preliminary Report of Patentability with Written Opinion of the International Searching Authority dated Feb. 3, 2013 in connection with International Application No. PCT/EP2011/063286.

Zhang et al. in Synapse 15(4):276- 284 (1993), Abstract.

International Preliminary Report of Patentability with Written Opinion of the International Searching Authority dated Jun. 21, 2016 in connection with International Application No. PCT/EP2014/077996.

International Preliminary Report of Patentability with Written Opinion of the International Searching Authority dated Jun. 21, 2016 in connection with International Application No. PCT/EP2014/077992.

International Preliminary Report of Patentability with Written Opinion of the International Searching Authority dated Jun. 4, 2013 in connection with International Application No. PCT/EP2011/071584.

International Preliminary Report of Patentability with Written Opinion of the International Searching Authority dated Jun. 26, 2012 in connection with International Application No. PCT/EP2012/059232.

International Preliminary Report of Patentability with Written Opinion of the International Searching Authority dated Mar. 15, 2016 in connection with International Applications No. PCT/EP2014/069370.

International Preliminary Report of Patentability with Written Opinion of the International Searching Authority dated May 30, 2012 in connection with International Application No. PCT/EP2010/068256.

International Preliminary Report of Patentability with Written Opinion of the International Searching Authority dated Nov. 27, 2012 in connection with International Applications No. PCT/EP2011/058224.

International Preliminary Report of Patentability with Written Opinion of the International Searching Authority issued on Oct. 26, 2010 in connection with International Application No. PCT/EP2009/054974.

International Preliminary Report of Patentability with Written Opinion of the International Searching Authority dated Oct. 20, 2015 in connection with International Application No. PCT/EP2014/057608.

International Search Report dated Jun. 17, 2009 in connection with International Application No. PCT/EP2009/054974.

International Search Report dated Jul. 24, 2009 in connection with International Application No. PCT/EP2009/054981.

(56) References Cited

OTHER PUBLICATIONS

International Search Report dated Jan. 31, 2012 in connection with International Application No. PCT/EP2011/063286.
International Search Report dated Apr. 5, 2011 in connection with International Application No. PCT/EP2011/051644.
International Search Report dated Nov. 25, 2010 in connection with International Application No. PCT/EP2010/061720.
International Search Report dated May 4, 2011 in connection with International Application No. PCT/EP2011/051630.
International Search Report dated Aug. 31, 2011 in connection with International Application No. PCT/EP2011/063583.
International Search Report dated May 4, 2011 in connection with International Application No. PCT/EP2010/068256.
International Search Report dated Sep. 21, 2011 in connection with International Application No. PCT/EP2011/058633.
International Search Report dated Feb. 25, 2015 in connection with International Application No. PCT/EP2014/077996.
International Search Report dated Jan. 12, 2005 in connection with International Application No. PCT/EP2005/009375.
International Search Report dated Jan. 16, 2012 in connection with International Application No. PCT/EP2001/071583.
International Search report dated Jul. 7, 2009 in connection with International Application No. PCT/EP2009/001109.
International Search Report dated Jun. 26, 2012 in connection with International Application No. No. PCT/EP12/59232.
International Search Report dated Mar. 13, 2012 in connection with International Application no. PCT/EP2011/071584.
International Search Report dated Mar. 23, 2011 in connection with International Application No. PCT/EP2010/068213.
International Search Report dated Mar. 6, 2014 in connection with International Application No. PCT/EP2014/057608.
International Search report dated May 23, 2011 in connection with International Application No. PCT/ EP11/51643.
International Search report dated Oct. 31, 2014 in connection with International Application No. PCT/EP2014/069370.
International Search report dated Sep. 17, 2014 in connection with International Application No. PCT/EP2014/063360.
International Search Report dated Sep. 3, 2015 in connection with International Application No. PCT/EP2014/077992.
International Search Report dated Mar. 8, 2011 in connection with International Applications No. PCT/EP2011/058224.
International Preliminary Report of Patentability with Written Opinion of the International Searching Authority dated Oct. 26, 2010 in connection with International Application No. PCT/EP2009/054981.
Isakov "The problem of pain in oncology", Russian Medicinal Journal, 2000, vol. 17, pp. 723-727.
Isomers [on-line], [retrieved on Mar. 11, 2007]. Retrieved from the Internet, URL: http://chemed.chem. purdue.edu/genchem/topicreview/bp/1organic/isomers .html>.
Izenwasser, S., et al., "Characterization of kappa-opioid receptor binding in human insular cortex", Life Sciences, Pergamon Press, Oxford, GB, vol. 65, No. 9, Jul. 23, 1999, pp. 857-862.
Janicki, et al., "Detection of Antagonist Activity for Narcotic Analgesics in Mouse Hot-Plate Test" Pharmacol. Biochem. Behavior, 1979; 10(4); pp. 623-626.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., *Neurotransmissions*; 1991; 7(1); 1-5.
Kautio, et al., "Amitriptyline in the Prevention of Chemotherapy-induced Neuropathic Symptoms" (2009) Anticancer Research, 29:2601-2606.
Kautio, et al., "Amitriptyline in the Treatment of Chemotherapy-Induced Neuropathic Symptoms" (2008) Journal of Pain and Symptom Management, 35(1) :31-39.

Kawamata, M., et al. "Experimental incision-induced pain in human skin: effects of systemic lidocaine on flare formation and hyperalgesia", Pain, 2002, vol. 100, pp. 77-89.
Kehlet, H., et al. "Persistent Surgical Pain: Risk Factors and Prevention," Lancet, 2006, vol. 367; pp. 1618-1625.
Kehlet, H., et al. "PROSPECT: evidence-based, procedure-specific postoperative pain management", Best Practice Res Clin Anaesthesiol., 2007, vol. 21, pp. 149-159.
Kehlet, H., et al., "Anaesthesia, surgery, and challenges in postoperative recovery", Lancet 2003, vol. 362, pp. 1921-1928.
Kadiroglu, A.K, et al., "The effect of venlafaxine HCl on painful peripheral diabetic neuropathy in patients with type 2 diabetes mellitus.", Journal of Diabetes and Its Complications Jul.-Aug. 2008, (Jul. 2008), vol. 22, No. 4, ISSN 1873-460X, pp. 241-245, XP002721925 [Y] 1-17 * Venlafaxine HCl is effective in the treatment of peripheral diabetic neuropathic pain *.
Kerba, et al. Oct. 2010, Journal of Clinical Oncology, vol. 28, No. 33, pp. 4892-4897.
Kest, et. al., Pharmacology Biochemistry, and Behavior, 1995, Pergamon, vol. 52, No. 1, pp. 175-178.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA-induced pain via PKC- and PKA-dependent phosphorylation of the NRI subunit in mice", Br. J. Pharmacal ., 2008, vol. 154, pp. 1125-1134.
Kim, et al., Int Neurourol J.; Mar. 2016; 20(1); 13-17.
Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2007, vol. 151 No. 1, pp. 69-75.
Kranz, H., et al., "Drug Release from MCC- and carrageenan-based pellets: Experiment and theory," European Journal of Pharmaceutics and Biopharmaceutics, 2009, vol. 73, pp. 302-309.
Kuloor, et. al., Age and Aging, 2006, Oxford University Press, vol. 35, pp. 639-640.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (Sep. 1, 2000), p. 389, (Sep. 1, 2000), XP027389705 [Y] 1-17. *Venlafaxine controlled release is effective in the treatment of pain *.
Kuruvilla et al., Arch Otolaryngol Head Neck Surg. Jan. 2009; 135(1 ): 101-105.
Laboratoire Roger Bellon's CAS: 87: 5959, 1977.
LaBuda, et al., (2005) Pharmacological evaluation of the selective spinal nerve ligation model of neuroFathic pain in the rat. J. Neurosci. Methods 144 ( 2) : 175-181.
LaBudde, et al., "The Synthesis of the Mono- and Dihydroxy Derivatives of 1 ,2,5,6-Dibenzanthracene Excreted by the Rabbit and of Other Hydroxylated Dibenzanthracene Derivatives", J. Am. Chem. Soc., 80, pp. 1225-1236, 1958.
Lagna, et al., "Generation and phenotypic analysis of sigma receptor type I (σ1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection," Journal of the American Chemical Society, 2002, vol. 124, No. 50, pp. 14834-14835, SI-S2.
Lau, et al. ( 2010) Electroacupuncture versus celecoxib for neuropathic pain in rat SNL model. Neuroscience 170 (2): 655-661.
Le Bars, D., et al., Animal models of nociception. *Pharmacal. Rev.* 2001; 53, 597-652.
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265-266, 282-283.
Levine, J.D. et al., "Desiperamide Enhances Opiate Postoperative Analgesia", Pain, 1986, vol. 27, pp. 45-49.

(56) References Cited

OTHER PUBLICATIONS

Li, et al.,"Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et al.,"Synthesis and Structure-Antitumor Activity of 4,6-Diamino-1 ,2-Dihydro-2,2-Dimethyi-1-(Substituted Naphthyi-2)-1,3,5-Triazines", Chern. Res. Chinese Univ., 7(3), pp. 197-200, 1991.
Li, F., et al., "Taurine reverses neurological and neurovascular deficits in Zucker diabetic fatty rats," Neurobiology of Disease, vol. 22, 2006, pp. 669-676.
Lowry, et al., "Protein measurement with the folin phenol reagent," J. Bio.Chem, 1951, vol. 193, pp. 265-275.
Luedtke, R. R., et al., "Neuroprotective effects of high affinity Sigma 1receptor selective compounds," Brain Res. Mar. 2, 2012;1441:17-26.
Luger N.M., et al., "Efficacy of systemic morphine suggests a fundarnen tal difference in the mechanisms that generate bone cancer vs. inflammatory pain", Pain 2002, vol. 99, pp. 397-406.
Luger, N.M., et al., "Bone Cancer Pain: From Model to Mechanism to Therapy", J. Pain and Symp. Manag. 2005, vol. 29 pp. 832-846.
Mantyh, "Bone cancer pain: From mechanism to therapy", Opin. Support. Palliat. Care, 2014, vol. 8, pp. 83-90.
Mar. 1, 2016 Fourth Office Action, issued in connection with Chinese Patent Application No. 201180065232 .X, including English language translation.
Mar. 29, 2016 Office Action, issued in connection with Japanese Patent Application No. 2013-541369, including English translation.
Marks, D.M., et al., "Serotonin-Norepinephrine reuptake inhibitors for pain control: Premise andpromise", Current Neuropharmacology, 2009, 7, pp. 331-336.
Maryanoff, B.E., et al., The Wittig Olefination Reaction and Modifications Involving Phosphoryl-Stabilized Carbanions. Stereochemistry, Mechanism, and Selected Synthetic Aspectsu, Chern. Rev., 1989, vol. 89, pp. 863-927.
Maurice, T., Su, T. P., The pharmacology ofSigma-1 receptors. *Pharmacal. Ther*. 2009; 124, 195-206.
Max, M.B., et al. "Endogenous Monoamine Analgesic Systems: Amitriptyline in Painful Diabetic Neuropathy", Anesth. Prog., 1987, vol. 34, pp. 113-127.
McGill, J.B., et al., "13-Biocker use and diabetes symptom score: results from the GEMINI study", Diabetes, Obesity and Metabolism, vol. 9, No. 3, May 2007, pp. 408-417.
Mega, et al., Experimental Diabetes Research, Jan. 12, 2011, Diabetic Nephropathy Amelioration by a Low-Dose Sitagliptin in an Animal Model of Type 2 Diabetes (Zucker Diabetic Fatty Rat).
Menten, J., "Co-analgesics and adjuvant medication in opioid treated cancer pain", Eur. J. Cancer Supplement 2005, vol. 3, pp. 77-86.
Ming, L.C., "Screening Polymorphic Forms of Drug Substances by Using Generalized Crystallization Techniques," May 2007 (English language Translation of Abstract).
Moncada A., et al., Effects of serine/threonine protein phosphatase inhibitors on morphine-induced antinociception in the tail flick test in mice. *Eur J Pharmacal*. 2003; Mar. 28; 465(1-2): 53-60.
Mosandl, et al., "Stereoisomeric Flavor Compounds XLIV: Enantioselective Analysis of Some Important Flavor Molecules", J. High Resol. Chromatog 13(9), pp. 660-662, 1990.
Mouedden, et al., "Pharmacological evaluation of opioid and non-opioid analgesics in a murine bone cancer model of pain", Pharm. Biochem. and Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is a major contributor to the antihyperalgesic effect of antidepressants after peripheral nerve injury in the rat. *Pain*. 2012; 153(5): 990.
Nakazato a., et al., "Synthesis and SAR of 1-alkyl-2-phenylethylamine derivatives designed from N,Ndipropyl-4-methoxy-3-(2-phenylethoxy) phenylethylamine to discover ?1ligands", J. Med. Chem., (1999), vol. 42, pp. 3965-3970.
Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.
Nieto, F.R., et al., "Tetrodotoxin inhibits the development and expression of neuropathic pain induced by paclitaxelin mice", Pain, 2008, vol. 137, pp. 520-531.
Niiyama, et al., "SB366791, a TRPVI antagonist, potentiates analgesic effects of systemic morphine in a murine model of bone cancer pain", Br. J. Anaesth., 2009, vol. 102, pp. 251-258.
Noda, et al., "A Neuroactive Steroid, Dehydroepiandrosterone Sulfate, Attenuates the Development of Morphine Dependence: an Association with Sigmal Receptors," Neuroscience 2001 Abstract, Presentation No. 668.4, Nov. 2001.
Nomura, M., et al., "Studies on drug dependence (Rept 322): Attenuation of morphine- and psychostimulants-induced place preference by sigmal receptor agonist SA4503", Japanese Journal of Pharmacology, the Japanese Pharmacological Society, Kyoto, JP, vol. 79, No. suppl. 1, Jan, 1, 1999, p. 224P.
O'Brien, C. J., "Recycling the Waste: The Development of a Catalytic Witting Reaction", Agnew. Chern. Int. Ed. 2009, vol. 48, pp. 6836-6839.
Office Action and Search Report corresponding to Taiwanese Patent Application No. 100127236 (Translation) [undated].
Office Action dated Mar. 18, 2013 in connection with Russian Patent Application No. 2010138634, filed Feb. 17, 2009.
Official Action corresponding to Japanese Patent Application No. 2013-523580, dated Mar. 31, 2015.
Ohsawa, et al.,"Effect of acute topical application of(+)-pentazocine on the mechanical allodynia in. diabetic mice" Eur. J. Pharmacal., 2010, 641, pp. 49-53.
Olivar, T., et al.,"Cyclophosphamide cystitis in mice: behavioural characterisation and correlation with bladderinflammation", European Journal of Pain, 3, 1999, pp. 141-149.
Oltman, C.L., et al., "Progression of vascular and neural dysfunction in sciatic nerves of Zucker diabetic fatty and Zucker rats", Am. J. Physiol. Endocrinol. Metab., vol. 289, 2005, pp. E113-E122.
Oltman, C.L., et al., "Vascular and neural dysfunction in Zucker diabetic fatty rats: a difficult condition to reverse", Diabetes, Obesity and Metabolism, vol. 10, 2008, pp. 64-74.
Oltman, et al., "Treatment of Zucker diabetic fatty rats with AVE7688 improves vascular and neural dysfunction", Diabetes, Obesity and Metabolism, vol. 11, No. 3, 2009, pp. 223-233.
O'Neill, J., et al., Unravelling the rnystery of capsaicin: a tool to understand and treat pain. Pharrnacol Rev. Oct. 2012;64(4) :939-71.
Ongioco, C. D., et al., Alpha2-adrenergic receptors in human dorsal root ganglia: predominance of alpha2b and alpha2c subtype mRNSs, *Anesthesiology* 2000; 92 (4): 968-976.
Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL <rmj.ru/number.36.htm).
Otto, et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months."
Pacharinsak,C., et al., ' "Animal Models of Cancer Pain", Comparative Medicine, 2008, vol. 58, No. 3, pp. 220-233.
Paice, J. A., "Clinical Challenges: Chemotherapy-induced Peripheral Neuropathy", Seminars in Oncology Nursing, 2009, vol. 25, N. 2, Suppl 1, pp. S8-S19.
Perret, D., et al., "Targeting voltage-gated calcium channels for neuropathic pain rnanagernent", Neurotherapeutics: The Journal of the American Society for Experimental NeuroTherapeutics, vol. 6, Oct. 2009, pp. 679-692.
Petrie, C. et al., "A Novel Biotinylated Adenylate Analogue Derived from Pyrazolou3,4-D 3/4 Pyrimidine for Labeling DNA Probes"

(56) References Cited

OTHER PUBLICATIONS

Bioconjugate Chemistry, ACS, Washington, DC, US LNKD—DOI:10.1021/BC00012A011, vol. 2, No. 6, Nov. 1, 1991 (Nov. 1, 1991), pp. 441-446, XP0005727891SSN: 1043-1802.

Pirim, A., et al., "Addition of ketamine infusion to patient controlled analgesia with intravenous morphine after abdominal hysterectomy" Agri Jan. 2006; 18(1):52-8 Abstract.

Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (Mar. 1, 2006), vol. 29, No. 2, suppl, ISSN 0162-220X, pp. 39-47, XP009107315 [A] 1-16 * p. 41, col. R, paragraph 2 ** p. 42, col. R, paragraph 2 *.

Poncelet, A.N., "Risk factors, patterns of presentation, diagnosis, and treatment", Geriatrics, vol. 58, No. 6, Jun. 2003, pp. 16-18, 24-30.

Postma, T.J., et al., "Paclitaxel-induced neuropathy," Annals of Oncology, 1995, vol. 6, pp. 489-494.

Price, et al., J. Am. Chem. Soc., (2005), vol. 127, p. 5512.

Prodrug [online], [retrieved on Mar. 11, 2007. Retrieved from the Internet, URL: http://en.wikipedia.org/wiki/Prodrug>.

Puente, B., et al., "Sigma-1 receptors regulate activity-21 induced spinal sensitization and neuropathic pain after peripheral nerve injury", Pain, 2009, vol. 145, pp. 294-303.

Puskas, F.,et al., Intrathecal clonidine and severe hypotension after cardiopulmonary bypass, *Anesth Analg.* 2003; 97 (5): 1251-1253.

Quasthoff, S., et al., "Chemotherapy-induced peripheral neuropathy," J Neural., 2002, vol. 249, pp. 9-17.

Radesca, et al., "Synthesis and Receptor Binding of Enantimeric N-Substituted cis-N-[2(3,4 Dishlorophenyl)ethyl]-2-(1-pyrrolidinyl)cyclohexylamines as High-Affinity σReceptor Ligands," J. Med. Chem., 1991, vol. 34, pp. 3058-3065.

Rao, R.D., et al., "Efficacy of Lamotrigine in the Management of Chemotherapy-induced Peripheral Neuropathy placebo-controlled trial, N01C3", Cancer; 2008, 112(12), 2802-2808.

Receveur, Jean-Marie, et al., "Synthesis and biological evaluation of conformationally restricted gabapentin analogues", Bioorganic & Medicinal Chemistry Letters, 9, 1999, pp. 2329-2334.

Reuben, S. S., et al., "Evaluation of efficacy of the perioperative administration of venlafaxine XR in the prevention of postrnastectorny pain syndrome", Journal of Pain and Syrnptorn Management, Feb. 2004, vol. 27, No. 2, pp. 133-139.

Rodriguez-Spong, B., et al., "General principles of pharmaceutical solid polymorphism: a supramolecular Perspective," Advanced Drug Delivery Reviews, vol. 56 (2004) pp. 241-274.

Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.

Romero, L., et al., J. Pharmacological properties of Sira, a new Sigma-1 receptor antagonist that inhibits neuropathic pain and activity-induced spinal sensitization. *Br. J. Pharmacal.* 2012; doi: 10.1111/j.1476-5381.

Roos, et al., Radiotherapy and Oncology, 2003, vol. 67, pp. 207-212.

Rossiter, et al., "Copper (H)-Mediated Arylation with Aryl Boronic Acids for the N-Derivatization ofPyrazole Libraries," J. Comb. Chern., 2004, vol. 6, pp. 385-390, published on web Feb. 5, 2004.

Rouleau, A., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.

Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.

Rowinsky, E.K., et al., "Clinical Toxicities Encountered 24 with Paclitaxel (TAXOL)", Seminars in Oncology, 1993, vol. 20, No. 4, suppl. 3, pp. 1-15.

Sabetkasaie, M., et al., "Clonidine and guanfacine-induced antinociception in visceral pain: possible role of alpha2/I2 binding sites", European Journal of Pharmacology, Elsevier Science, NL, (Oct. 6, 2004), vol. 501, No. 1-3, doi:10.1016/J.EJPHAR.2004.08.010, ISSN 0014-2999, pp. 95-101.

Saha, et al., "Spinal Mitogen-Activated Protein Kinase Phosphatase (MKP-3) Is Necessary for the Normal Resolution of Mechanical Allodynia in a Mouse Model of Acute Postoperative Pain", J.Neurosci., 2013, vol. 43, pp. 17182-17187.

Said, G., "Diabetic Neuropathy", Proceedings advanced studies in Medicine, vol. 1, No. 11, Dec. 2001, pp. 457-459.

Sakurada T., et al., Differential effects of intraplantar capsazepine and ruthenium red on capsaicin-induced desensitization in mice. Pharmacal Biochern Behay. Apr. 2003; 7 5 (1): 1 15-21.

Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, XP009169909 [Y] 1-15 * See abstract: imidazoline I2 receptor ligands have antinociceptic effect in acute pain *.

Samso, E., et al., Comparative assessment of the anaesthetic and analgesic effects of intramuscular and epidural clonidine in humans, *Can J Anaesth.* 1996; 43 (12): 1195-1202.

Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.

Sandford, M., et al., Pain Physician 2009; 12:679-684.

Sant et al., "The mast cell in interstitial cystitis: role in pathophysiology and pathogenesis,"Urology, 69, Suppl 4A, 2007, pp. 34-40.

Schiff, et al., Nature vol. 277 pp. 665-667. Publication date: Feb. 22, 1979.

Schlegel, T., et al., "Responsiveness of C-fiber nociceptors to punctate force-controlled stimuli in isolated rat skin: lack of modulation by inflammatory mediators and flurbiprofen" Neuroscience Letters, vol. 361, 2004, pp. 163-167.

Xu, J. et al., Identification of the PGRMCI protein complex as the putative sigma-2 receptor binding site. Nat Comnun. Jul. 5, 2011; 2:380.

Schoeffter, et al., "Functional, endogenously expressed 5-hydroxytryptamine 5-ht7 receptors in human vascular smooth muscle cells," British Journal of Pharmacology, 1996, vol. 117, pp. 993-994.

Schreiber, S., et al., "The antinociceptive effect of venlafaxine in mice is mediated through opioid and adrenergic mechanisms", Neuroscience Letters, Limerick, IE, (Jan. 1, 1999), vol. 273, doi: 10.1016/50304-3940(99)00627-8, ISSN 0304-3940, pp. 85-88, XP003009174 [Y] 1-17 * Venlafaxine has antinociceptive effects and is effective for treating pain. *.

Gotub et al., "Molecular Classification of Cancer: Class Discovery and Class Prediction by Gene Expression Monitoring," Science, 286: 531-537, 1999.

Sevcik, M.A., et al., "JInti-NGF therapy profoundly reduces bone cancer pain and the accompanying increase in markers of peripheral and central sensitization", Pain 2005, vol. 115, pp. 128-141.

Shaw, et al., Proc. Soc. Exp. Biol. Med., (1983), vol. 173, No. 1, pp. 68-75.

Shen, D.M., et al., "Versatile and Efficient Solid-Phase Syntheses of Pyrazoles and Isoxazoles", Organic Letters, 2000, vol. 2, No. 18, pp. 2789-2792.

Shimizu, I., et al., "Effects of AH-9700, (+)-pentazocine, DTG and oxybutynin on micturition in anesthetized rats with acetone-induced cystitis", Life Sciences 69,2001, pp. 1691-1697.

Shimoyama, E., et al., Integrative Medicine you Need to know now "Cancer and Integrative Medicine Palliative Medicine", Modern Physician, Nov. 2008, vol. 28, No. 11, pp. 1605-1607 [inc. machine English language translation].

Shu, et al., "Parameter Effects on the Thermal Reaction of Cystine and 2,5-Dimethyl-4-hydroxy-3(2H)-furanone", ACS Symposium Letters, 409, pp. 229-241, 1989.

Shvidenko, K.V., et al., "Recyclization Reactions of 2-(1-Benzoylpyrrolidin-2-Ylidene)Malononitrile", 2010, vol. 46, No. 1, pp. 56-60.

(56) References Cited

OTHER PUBLICATIONS

Siau, C., et al., "Dysregulation of Cellular Calcitt.rn Homeostasis in Chemotherapy-Evoked Painful Peripheral Neuropathy", *Anest:h Analg.*, 2006, 102(5), pp. 1485-1490.
Sierralta, F., et al., Alpha-Adrenoceptor and opioid receptor modulation of clonidine-induced antinociception, *Br J Pharmacal.* 1996; 119 (3): 551-554.
Sima, A.A.F., "The heterogeneity of diabetic neuropathy", Frontiers in Bioscience, May 2008, pp. 4809-4816.
Sima, A.A.F., et al., "A comparison of diabetic polyneuropathy in Type II diabetic BBZDR/Wor rats and in Type I diabetic BBNVor rats", Diabetologia, vol. 43, 2000, pp. 786-793.
Smith, et al., Life Sci., (2004), vol. 74, No. 21, pp. 2593-2604.
Snyder, et al., "Receptor Mechanisms in Antipsychotic Drug Action: Focus on Sigma Receptors," Journal of Neuropsychiatry, Winter 1989, Vol , No. 1, pp. 7-15.
Sonal, G., et al., Ther. Adv. Urol., (2011), vol. 3, No. 1, pp. 19-33,.
Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
Non-Final Office Action dated Feb. 2, 2009 in related U.S. Appl. No. 11/574,361 citing STN-search report report JP10055048 (p. 8).
Strupp, et al., "Transdermal fentanyl during high-dose chemotherapy and autologous stem cell support" (2000) Oncology Reports, 7:659-661.
Stubblefield, et al., "Upper-Extremity Pain Disorders in Breast Cancer" (2006) Arch Phys Med Rehabil, vol. 87, Suppl 1, pp. 596-S99.
Su, et al., Pharmacology & Therapeutics, vol. 124, pges 195-206, 2009.
Sussman, N., "SNRis versus SSRis: Mechanisms of action in treating depression and painful physical symptoms", Primary Care Companion J. Clin. Psychiatry, 2003, 5 (suppl 7), pp. 19-26.
Suzuki, Y., et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.
Tanda, S., et al., "Pains Resistant to Opioids, and Countermeasures thereof ~ Including Peripheral Neuropathy Measures of Oxaliplatin", Pharmacy, Oct. 2007, vol. 58, No. 11, pp. 2947-2953 [inc. machine English language translation].
Taylor, C.P., "Mechanisms of analgesia by gabapentin and pregabalin-calcium channel alpha2-delta [Ca v alpha2-delta]ligands", Pain, 142, 2009, pp. 13-16.
Telleria-Diaz, et al., Pain, 2010, 148, pp. 26-35.
Theoharides, T.C., "Mast cell involvement in interstitial cystitis: a review of human experimental evidence," Urology, (2001), vol. 57, No. 6, pp. 47-55.
Tietze, L., et al., Synthesis, (11), 1079-1080, 1993.
Uchitel, O.D., et al., "Acute modulation of calcium currents and synaptic transmission by Gabapentinoids," Channels, 4:6, Nov./Dec. 2010, pp. 490-496.
Van De Merwe, J.P., et al., "Diagnostic criteria, classification, and nomenclature for painful bladder syndrome/interstitial cystitis: an ESSIG proposal", European Urology, 53, 2008, pp. 60-67.
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 2012, 32 Suppl. 1, pp. 3-10.
Venturello, C., "2-Arylazo-2, 5-dimethyl-3-oxo-2, 3-dihydrof urans, useful intermediates in the synthesis of 1-aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions 1: Organic and Bio-organic Chemistry, (1972-1999), 7, 681-685, 1978.

Vileikyte, L., et al., Psychological aspects of diabetic neuropathic foot complications: an overview, Diabetes /Metabolism Research and Reviews, 2004, vol. 20 (Suppl1), pp. S13-S18.
Vinik, A., et al., Nature Clinical Practice Endocrinology & Metabolism, (2006), vol. 2, pp. 2-13.
Vippagunta, et al., Crystalline solids, Advanced Drug Delivery Reviews, 48: 1-26, 2001.
Virmani, et al., Indian Journal of Chemistry, Section B:Organic Chemistry Including Medicinal Chemistry,vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database accession No. 705147, XP002605613 [X] 1-3,9 * the whole document *.
Virmani, V. et al., "Methyl-{4-[5-(4-nitro-phenyl)-1-phenyl-1H-pyrazol-3-yl]-butyl}amine", Database Beilstein, Beilstein Institute for Organic Chemistry, Frankfurt-Main, DE, Database accession No. 706821, XP002605614 [X] 1-3,9 * the whole document *.
Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3,9 * the whole document *.
Vorobeychik, et al., "Combination Therapy for Neuropathic Pain—A Review of Current Evidence," CNS Drugs, 2011, pp. 1-12.
Wagaw, S. et al., "A Palladium-Catalyzed Strategy for the Preparation of Indoles: A Novel Entry Into the Fischer Indole Synthesis", J. American Chemical Society, 1998, vol. 120, pp. 6621-6622.
Walker, et al., "Sigma Receptors: Biology and Function," Pharmacological Review, 1990, vol. 42, No. 4, pp. 355-402.
Wantuch, C., et al., "Pharmacological validation of a model of cystitis pain in the mouse", Neuroscience Letters, 421, 2007, pp. 250-252.
Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.
Weetman, A.P., "Graves' hyperthyroidism: how long should antithyroid drug therapy be continued to achieve remission?," Nature Clinical Practice Endocrinology and Metabolism, vol. 2, No. 1, Jan. 2006, pp. 2-3.
Whittington, C.M., et al., Understanding and utilizing mammalian venom via a platypus venom transcriptome. J. Proteomics 2009; 72; 155-164.
Wickham, "Chemotherapy-Induced Peripheral Neuropathy: A Review and Implications for Oncology Nursing Practice" (2007) Clinical Journal of Oncology Nursing, vol. 11, No. 3, pp. 361-376.
Wild, S., et al., "Global Prevalence of Diabetes", Diabetes Care, vol. 27, No. 5, May 2004, pp. 1047-1053.
Wilkes, G. "Peripheral Neuropathy Related to Chemotherapy", Seminars in Oncology Nursing, 2007, vol. 23, 3. pp. 162-173.
Wilson, S. G., "The heritability of antinociception: common pharmacogenetic mediation of five neurochemically distinct analgesics," *J Pharmacal Exp Ther*. 2003; 304 (2): 547-559.
Winkler, et al., "Synthesis of Highly Functionalized Furanones via Aldol Reaction of 3-Silyloxyfurans", Organic Letters, vol. 7, No. 3, pp. 387-389, 2005.
Wolf, S., et al., "Chemotherapy-induced peripheral neuropathy: Prevention and treatment strategies, " European Journal of Cancer, 2008, vol. 44, issue 11, pp. 1507-1515.
Wong, H.Y., et al., Pentarnorphone for Management of Postoperative Pain. Anesth Analg. 1991; 72:656-60.
Wu, et al., Regulatory Perspectives of Type II Prodrug Development and Time- Dependent Toxicity Management: Nonclinical Pharm/Tox Analysis and the Role of Comparative Toxicology, Toxicology, 236: 1-6, 2007.
Wunsch, et al., Journal Med. Chem. vol. 55, No. 19, pp. 8209-8210, 2012.
Xiaoping, et al., "Involvement of the spinal NMDA receptor/PKCy signaling 12 pathway in the development of bone cancer pain", Brain Research, 2010, vol. 1335, pp. 83-90.
Yaksh, T. L., Pharmacology of spinal adrenergic systems which modulate spinal nociceptive processing. *Pharmacal Biochem Behav.* 1985; 22(5): 845-58.

(56) References Cited

OTHER PUBLICATIONS

Yasuda, M., et al., "Mast Cell Stabilization Promotes Antinociceptive Effects in a Mouse Model of Postoperative Pain," J. Pain Res., 2013, vol. 6, pp. 161-166.

Yeretzian, et al., "Analysing the headspace of coffee by proton-transfer-reaction mass-spectrometry", Int J. Mass Spect, 223-224 (1-3), pp. 115-139, 2003.

Zahn, P.K., et al., "Mechanisms for Pain Caused by Incisions", Regional Anesthesia and Pain Medicine, 2002, vol. 271 No. 5, pp. 514-516.

Zheng, F.Y., et al. "The Response of Spinal Microglia to Chemotherapy Evoked Painful Peripheral Neuropathies Is Distinct From That Evoked by Traumatic Nerve Injuries," Neuroscience, 2011, 176, pp. 447-454.

Aapro, M. et al., "Anticipatory Nausea and Vomiting", Support Care Cancer, 2005, vol. 13, pp. 117-121.

Argyrioul A.A. et al., "Bortezomib-induced peripheral neuropathy in multiple myeloma: a comprehensive review of the literature", Blood, 2008, vol. 112, No. 5, pp. 1593-1599.

Barnes, J.M. et al., "Reserpine, Para-Chlorophenylalanine and Fenfluramine Antagonise Emesis i n Eesis the Ferret", Neuropharmacology, 1988, vol. 27, No. 8, pp. 783-790.

Brammer et al. In European Journal of Pharmacology, 553, 141-145 (2006).

Crawford, K.W. and Bowen, W. D., "Sigma-2 Receptor Agonists Activate a Novel Apoptotic Pathway and Potentiate Antineoplastic Drugs in Breast Tumor cell Lines/," Cancer Research, 2002, vol. 62, pp. 313-322.

Gralla et al. In Annals of Internal Medicine 95(4), 414-420 (1981).

Grunberg, S, M., et al., "Incidence of Chemotherapy-Induced Nausea and Emesis after Modern Antiemetics," Cancer, 2004, vol. 100, pp. 2261-2268.

Guitart, X., et al., "Sigma receptors biology and therapeutic potential", Psychophamacology, 2004, vol. 17 4, pp. 301-319.

Hanner et al., "Purification, molecular cloning, and expression of the mammalian sigma1-binding site," Proc. Natl. Acad. Sci., USA, Jul. 1996, vol. 93, pp. 8072-8077.

Hayashi, T., et al., "Sigma-1 receptor ligands: potential in the treatment of neuropsychiatric disorders," CNS Drugs. 2004;18(5):269-84.

Hecht, J. R. et al., "Prolonged Nausea and Vomiting after High Dose Chemotherapy and Autologous Peripheral Stem Cell Transplantation in the Treatment of High Risk Breast Carcinorrta," Cancer, 19971 vol. 7 9' pp. 1698-1702.

Herrstedt, J., et al., \'Acute emesis moderately emetogenic chemoc. herapy, Support Care Cancer, 2005, vol. 13, pp. 97-103.

Hesketh, M. M et al., "Proposal for classifying the Acute Emetogenicity of Cancer Chemotherapy", Journal of Clinical Oncology, 1997, vol. 15, pp. 103-109.

Hudzik T. J., "Sigma Ligand-Induced Emesis in the Pigeon," Pharmacology Biochemistry & Behavior, 1991, 41(1), pp. 215-217.

Hudzik, T., et al., "o Receptor-mediated emetic response in pigeons: agonists, antagonists and modifiers", European Journal of Pharmacology, 1993, vol. 236, pp. 279-287.

Jordan, K., et al. "Chemotherapy-induced nausea and vomiting: current and new standards in the antiemetic prophylaxis and treatment," Eur J Cancer. Jan. 2005;41 (2) :199-205.

Koralewski, p., et al., Effectiveness of cyproheptadine in the management of delayed vomiting after cisplatin-based chemotherapy and the assessment of the influence of cyproheptadine on quality of lifen, Chemotherapy Dept. Rydygier Memorial Hospital, Cracow, Poland, vol. 5, pp. 499-503.

Laggner et al. "Discovery of High-Affinity Ligands of Sigma Receptor, ERG2, and Emopamil Binding Protein by Pharmacophore Modeling and Virtual Screening", J. Med. Chem., 2005, vol. 48, pp. 4754-4764.

Lippincott's Illustrated Review: Pharmacology, Richard Harvey, 5th, edition published by Wolters Kluwer "Gastrointestinal and Antiemetic Drugs", pp. 351-362.

Matsumoto RR1, Pouw B. Correlation between neuroleptic binding to sigma(1) and sigma(2) receptors and acute dystonic reactions. Eur J. Phamacol. Aug. 4, 2000;401(2) :155-60.

Mielke, s. et al., "Peripheral neuropathy: a persisting challenge in paclitaxel-based regimes" / European Journal of Cancer, 2006, vol. 42, pp. 24-30.

Nausea and Vomiting (PDQ) Health Professional Version: Prevention and Managemenl of Acute or Delayed Nausea and Vomiting (Emesis). National Cancer Institute. <http://www.cancer.gov/about-cancer/treatment/sideeffects/nausea/nausea-hp-pdq#sectIon/-66>.

Owens, N.J. et al., "Antiemetic efficacy of prochlorperazine, haloperidol, and droperidol in cisplatin-induced emesis", Clinical Pharmacy, 1984, vol. 3, pp. 168-170.

Palmer, J. L., and Fisch, M. J., "Association Between Symptoms Distress and Survival in Outpatients Seen in a Palliative Care Caner Center", Journal of Pain and Symptom Management, 2005, vol. 29, No. 6, pp. 565-571.

Paquette et al. In Psychopharmacology (Berlin) 204(4):743-754 (2009).

Park, S.B. et al. "Mechanisms Underlying Chemotherapy-Induced Neurotoxicity and the Potential for Neuroprotective Strategies", Current Medicinal Chemistry, 2008, vol. 15, pp. 3081-3094.

Raynov, J, "Antiemetics: Side effects and reactions", Archive of Oncology, 2001, vol. 9, No. 3, pp. 151-153.

Roila, F. et al., "Delayed emesis: moderately emetogenic chemotherapy", Support Care Cancer, 2005, vol. 13, pp. 104-108.

Seigel, L.J., et al., The Control of Chemotherapy-Induced Emesis, Ann Intern Med. 1981;95(3) :352-359.

Selwood, D. L., et al. Synthesis and Biological Evaluation of Novel Pyrazoles and Indazoles as Activators of the Nitric Oxide Receptor, Soluble Guanylate Cyclase,J. Med. Chern, 2001, vol. 44,pp. 78-93.

Silvey et al. in Journal of Clinical Oncology 6(9), 1397-1400 (1988) (Abstract).

Smith, J.C. et al., "Haloperidol: An alternative butyrophenone for nausea and vomiting prophylaxis in anesthesia," AANA Journal 2005, vol. 73, No. 41 pp. 273-275.

Tramer, M. R., et al., "Efficacy and Adverse Effects of Prophylactic Anti emetics during Patient-Controlled Analgesia Therapy: A Quantitative Systematic Review, "Anesth. Analg., 1999, vol. 88, pp. 1354-1361.

Tyers et al. Oncology 49(4), 263-268 (1992) (Abstract).

Van Sickle et al. Gastroenterology 121 (4), 767-774 (2001) (Abstract).

\* cited by examiner

EXPERIMETAL PROTOCOL N°1 (PERIOPERATIVE ADMINISTRATION)

EXPERIMETAL PROTOCOL N°3 (COADMINISTRATION IN NAÏVE RATS)

EXPERIMENTAL PROTOCOL N°2 (OIH precipitated by naloxone)

- ■ Vehicle + NALOXONE
- Vehicle + REMIFENTANIL + NALOXONE
- ● Compound 63 (20mg/kg) + REMIFENTANIL + NALOXONE
- ▼ Compound 63 (40mg/kg) + REMIFENTANIL + NALOXONE
- ▲ Compound 63 (80mg/kg) + REMIFENTANIL + NALOXONE

USE OF SIGMA LIGANDS IN OPIOID-INDUCED HYPERALGESIA

CROSS-REFERENCE TO RELATED APPLICATIONS

This application is filed under the provisions of 35 U.S.C. §371 and claims the priority of International Patent Application No. PCT/EP2011/063286 filed on Aug. 2, 2011, and of European Patent Application No. 10382215.1 filed on Aug. 3, 2010. The disclosures of the foregoing international patent application and European patent application are hereby incorporated by reference herein in their respective entireties.

FIELD OF THE INVENTION

The present invention relates to the use of sigma receptor ligands in the prevention and/or treatment of opioid-induced hyperalgesia (OIH) associated to opioid therapy, including the combination of opioids with a sigma receptor ligand for the treatment and/or prevention of OIH.

BACKGROUND

Opioids and opiates are potent analgesics widely used in clinical practice. Opiates refer to alkaloids extracted from poppy pods (Opium Poppy; *Papaver Somniferum*) and their semi-synthetic counterparts which bind to the opioid receptors. Basically to be called an opiate one has to either be a natural opioid receptor agonist or start the refining process with one of the natural alkaloid molecules. Once chemically altered, such as the process of converting morphine into heroin, the drug is then labeled as a semi-synthetic opiate or semi-synthetic opioid—the terms can be used interchangeably. Semi-synthetic opiates (or semi-synthetic opioids) include heroin (diamorphine), oxycodone, hydrocodone, dihydrocodiene, hydromorphone, oxymorphone, buprenorphine and etorphine. In contrast, opioid is a blanket term used for any drug which binds to the opioid receptors. Opioids include all of the opiates as well as any synthesized drug that bind to opioid receptors. Synthetic opioids include methadone, pethidine, fentanyl, alfentanil, sufentanil, remifentanil, carfentanyl, tramadol, tapentadol and loperamide.

Opioid and opiates drugs are classified typically by their binding selectivity in respect of the cellular and differentiated tissue receptors to which specific the drug binds as a ligand. There are 3 well-defined or "classical" types of opioid receptor: mu (μ), delta (δ), and kappa (κ). More recently, cDNA encoding an "orphan" receptor named ORL1 (opioid receptor-like) was identified which has a high degree of homology to the "classical" opioid receptors. All the opioid receptors are G-protein coupled receptors and possess the same general structure: an extracellular N-terminal region, seven transmembrane domains and an intracellular C-terminal tail structure. Pharmacological evidence supporting for subtypes of each receptor and other types of novel, less well-characterised opioid receptors have also been postulated. The well-known opioid analgesics bind to and activate selectively the opioid mu receptors; that is, they act as agonists at mu opioid receptors. The sigma receptor, however, is not regarded as an opioid receptor.

Opioid analgesics are recommended for the management of moderate to severe pain including that which occurs following surgery and trauma and in many patients with cancer. Apart from pain relief, opioid analgesics also produce a range of common well-known side effects (e.g., sedation, emesis, constipation, respiratori depression, dependence).

In addition to the afore-mentioned side-effects, it has been appreciated more recently that opioid analgesics may also activate a pro-nociceptive mechanism resulting in the phenomenon of opioid-induced hyperalgesia (OIH) [also called opioid-induced abnormal pain sensitivity]. OIH is a recognized complication of opioid therapy characterized by enhanced pain sensitivity. Somewhat paradoxically, opioid therapy aiming at alleviating pain may render patients more sensitive to pain and potentially may aggravate their preexisting pain. In fact, OIH should be considered in the differential when opioid therapy fails. Hence, any apparent decrease in opioid analgesic effectiveness may be due at least in part to the presence of OIH rather than reflecting a worsening of the disease state and/or the development of pharmacological tolerance.

As disclosed in the art (Sandford, M. et al.; Pain Physician 2009; 12:679-684) the existence of OIH is proved by basic science evidence (Mao, J.; Pain 2002; 100:213-217) and by clinical evidence (Guignard, B. et al.; Anesthesiology 2000; 93:409-417 and Angst, M. S. et al.; Anesthesiology 2006; 104:570-587). Additionally there are neurobiological mechanisms discussed for OIH involving the central glutaminergic system, the spinal dynorphins or the descending facilitation.

OIH is evidenced by individuals taking opioids, which can develop an increasing sensitivity to noxious stimuli (hyperalgesia), even evolving a painful response to previously non-noxious stimuli (allodynia). Increased pain in OIH may result from one or more of the following: pain in the absence of a noxious stimulus (spontaneous pain), increased duration of pain in response to brief stimulation (ongoing pain or hyperpathia), reduced pain threshold (allodynia), increased responsiveness to suprathreshold stimulation (hyperalgesia), spread of pain and hyperalgesia to uninjured tissue (referred pain and secondary hyperalgesia), and abnormal sensations (e.g., dysesthesia, paresthesia).

OIH is a phenomenon often associated with the long term use of opioids, but some studies have demonstrated that this effect can also occur after only a single dose of opioids (E. Celerier et al., J. Neurosci. 21, 4074-4080 (2001)). Thus, OIH occurs following both acute and chronic opioid administration. In this way, OIH is a less recognized side effect of chronic opioid therapy. However, it is becoming more prevalent as the number of patients receiving opioids for chronic pain increases (Trescot, A. M. et al.; Pain Physician 2008; 11:S12-S16).

Increases in pain intensity can occur upon discontinuation of opioid therapy but such an abnormal increased pain sensitivity including hyperalgesia or allodynia can occur also in the absence of overt opioid withdrawal in subjects that have been administered opioid drugs.

The cellular mechanisms underpinning OIH have been proposed to be in common with those of neuropathic pain and analgesic tolerance involving augmented glutamatergic signaling and persistent activation of the N-methyl-D-aspartate (NMDA)-nitric oxide synthase (NOS)-nitric oxide (NO) signaling cascade.

Another mechanism proposed to underpin opioid-induced excitatory signaling involves stimulation of adenylate cyclase formation via $G_s$-coupled opioid receptors that opposes inhibition of adenylate cyclise formation via $G_{i/o}$-coupled opioid receptors to attenuate levels of pain relief (Smith, M. T.; Acute Pain 2008; 10:199-200).

It is known that the combination of opioid analgesics with agents that block excitatory opioid signaling pathways can improve pain relief. Some strategies include combining opioid analgesics with NMDA-receptor antagonists, such as low dose ketamine, and more recently, clinical trials have investigated combinations of ultra-low dose naltrexone (non-selective opioid antagonist) and opioid agonists such as morphine and oxycodone to selective block signaling via $G_s$-coupled opioid receptors (Smith, M. T.; Acute Pain; 2008; 10; 199-200) that are useful in the prevention and/or treatment of opioid-induced hyperalgesia.

Sigma receptors are non-opioid receptors of great interest in pharmacology. The sigma binding sites have preferential affinity for the dextrorotatory isomers of certain opiate benzomorphans, such as (+)SKF 10047, (+)cyclazocine, and (+)pentazocine and also for some narcoleptics such as haloperidol. The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

It has been reported that some sigma receptor ligands (i.e., haloperidol) in combination with opioids are capable of modulating the analgesic effect of opioids (both kappa and mu opiods) in models of acute thermal nociceptive tests (i.e., radiant heat tail-flick test) in mice (Mei J and Pasternak G W, Sigma 1 receptor modulation of opioid analgesia in the mouse, J Pharmacol Exp Ther. 2002, 300(3):1070-1074) and rats (Chien C C and Pasternak G W, Sigma antagonists potentiate opioid analgesia in rats, Neurosci Lett. 1995, 190(2):137-139). Recently it has been shown that some sigma-1 receptor antagonists potentiate opioid analgesia in models of acute thermal nociceptive pain and that this potentiation of analgesia is not accompanied by potentiation of opioid side effects (i.e., dependence) (WO 2009/130310). However, no information is available regarding inhibition of OIH by sigma-1 receptor ligands.

The treatment of OIH can be time-consuming and, at times, impractical. Weaning patients from high dose opioids usually requires time and patience. While reducing the opioid dose, patients may experience transient increases in pain or exacerbation of pain and the hyperalgesic effect may not be mitigated until a certain critical dose of opioid is reached.

Breaking the cycle of OIH is an attractive course of action for the interventional pain specialist. Thus, there is still a need for substances that could be used as an adjuvant to opioid therapy for the prevention and/or treatment of the associated OIH.

BRIEF DESCRIPTION OF THE INVENTION

The present invention relates to the use of a sigma ligand as adjuvant in the opioid therapy of pain for the prevention and/or treatment of OIH associated to said opioid therapy. This benefit of the invention is more evident when the sigma ligand is specifically a sigma-1 receptor antagonist, preferably in the form of a (neutral) antagonist, an inverse agonist or a partial antagonist.

Therefore, one aspect of the present invention relates to a sigma ligand for use in the prevention and/or treatment of OIH associated to opioid therapy.

In a preferred embodiment, said sigma ligand has the general formula (I):

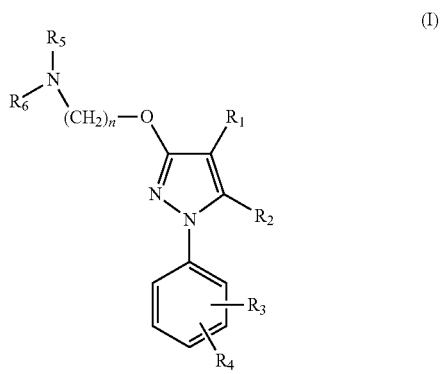

wherein
$R_1$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, and halogen;

$R_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, and halogen;

$R_3$ and $R_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, and halogen, or together they form an optionally substituted fused ring system;

$R_5$ and $R_6$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —CH=$NR_8$, —CN, —$OR_8$, —$OC(O)R_8$, —$S(O)_t$—$R_8$, —$NR_8R_9$, —$NR_8C(O)R_9$, —$NO_2$, —N=$CR_8R_9$, and halogen, or together form, with the nitrogen atom to which they are attached, a substituted or unsubstituted, aromatic or non-aromatic heterocyclyl group;

n is selected from 1, 2, 3, 4, 5, 6, 7 and 8;

t is 1, 2 or 3;

$R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, and halogen;

or a pharmaceutically acceptable salt, isomer, prodrug or solvate thereof.

Another aspect of this invention refers to the use of sigma ligand as defined above for the manufacture of a medicament for the prevention and/or treatment of OIH associated to opioid therapy.

Another aspect of the invention is a method of treatment of a patient suffering from OIH associated to opioid therapy, which comprises administering to the patient in need of such a treatment or prophylaxis a therapeutically effective amount of a sigma ligand as defined above.

Another aspect of the invention refers to a combination of at least one sigma ligand as defined above and at least one opioid or opiate compound for simultaneous, separate or sequential administration, for use in the prevention and/or treatment of opioid-induced hyperalgesia associated to opioid therapy.

These aspects and preferred embodiments thereof are additionally also defined in the claims.

BRIEF DESCRIPTION OF THE FIGURES

FIGS. 2 and 3 show that administration of the sigma ligand in the perioperative period inhibits the development of mechanical allodynia when administered both before (Paradigm 1) and after (Paradigm 2) opiod administration. At 40 and 80 mg/kg the sigma ligand (compound n° 63) inhibits allodynia secondary to both surgery and opioid (Remifentanil) use (i.e., OIH). When compound n° 63 is administered at the dose of 20 mg/kg OIH is selectively blocked.

DETAILED DESCRIPTION OF THE INVENTION

Figure 1:
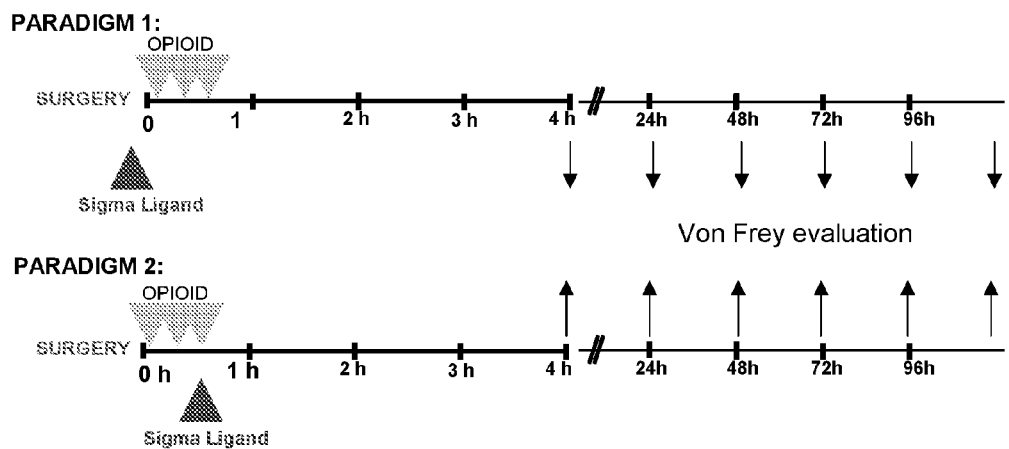
FIG. 1: Schematic representation of experimental protocol n° 1 (co-administration studies in the perioperative period) showing the time course for the assessment of mechanical sensitization induced by plantar incision. The opioid ligand was administered immediately after the surgery in three consecutive intraperitoneally injections (every 15 minutes). Paradigm 1 corresponds to a single administration of the sigma receptor ligand immediately before surgery and hence before opioid injection whereas Paradigm 2 corresponds to a single administration of the sigma receptor ligand immediately after the last opioid injection. The experimental protocol n° 1 represents a preventive approach as the sigma ligand is administered in the perioperative period (before-Paradigm 1 or immediately after-Paradigm 2 the opioid administration), long before hyperalgesia develops.
Figure 2:
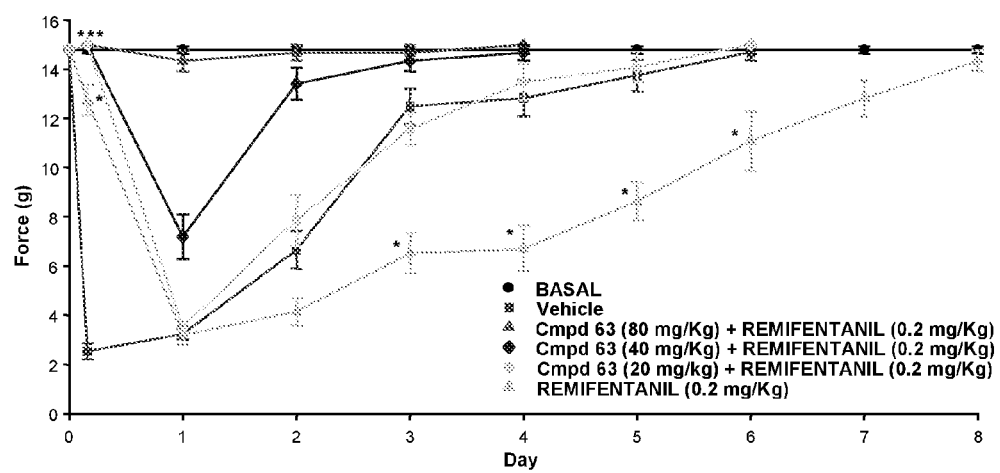
FIG. 2: It shows the effect of Remifentanil (opioid receptor agonist) and compound n° 63 (sigma antagonist) approached by Paradigm 1 according to experimental protocol n° 1 (co-administration studies in the perioperative period).
Figure 3:
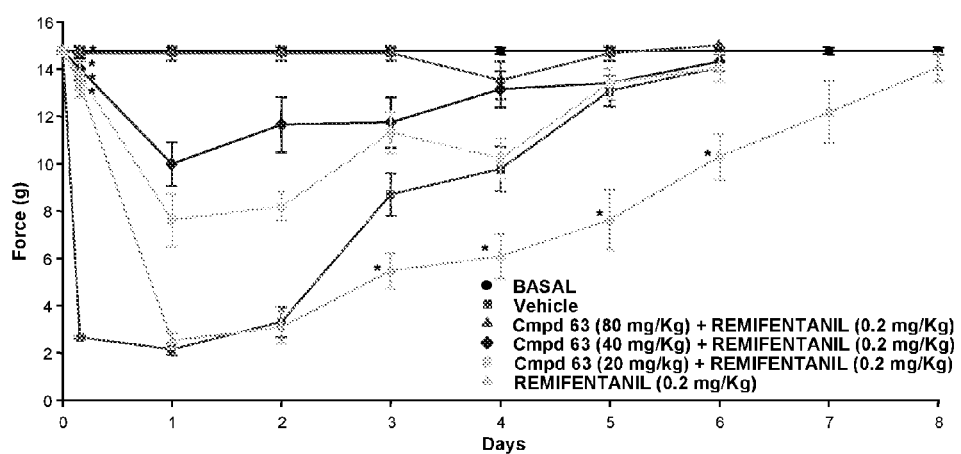
FIG. 3: It shows the effect of Remifentanil (opioid receptor agonist) and compound n° 63 (sigma antagonist) approached by Paradigm 2 according to experimental protocol n° 1 (co-administration studies in the perioperative period).
Figure 4:
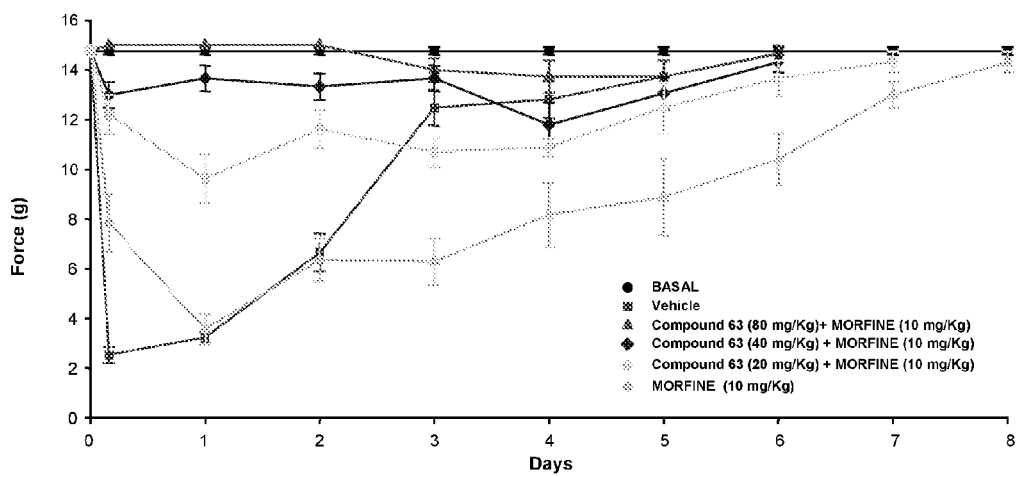
FIG. 4: It shows the effect of Morphine (opioid receptor agonist) and compound n° 63 (sigma antagonist) approached by Paradigm 2 according to experimental protocol n° 1 (co-administration studies in the perioperative period). Similar to previous figures showing the effect on Remifentanil use, the sigma ligand (compound n° 63) also inhibits allodynia secondary to surgery and OIH when Morphine was used.
Figure 5:
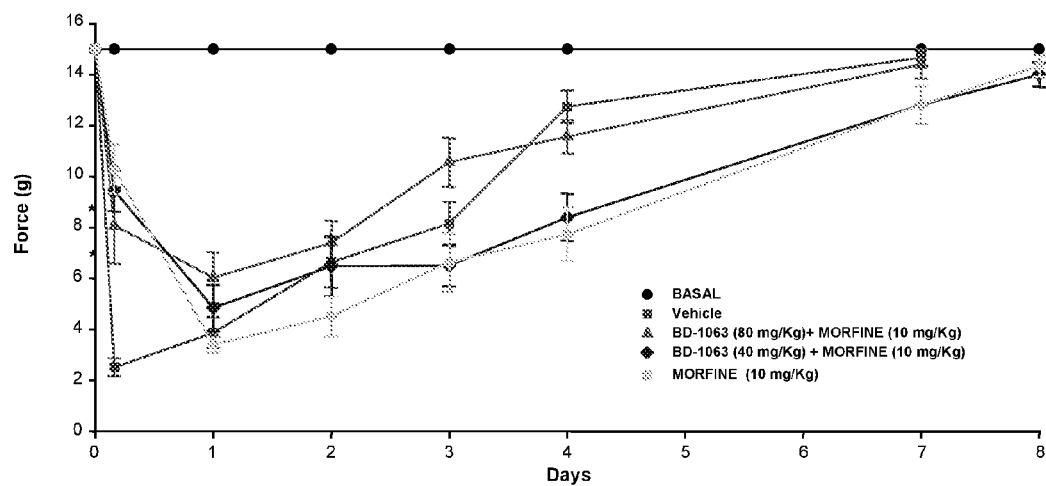
FIG. 5: It shows the effect of Morphine (opioid receptor agonist) and BD-1063 (sigma antagonist) approached by Paradigm 2 according to experimental protocol n° 1 (co-administration studies in the perioperative period). The sigma ligand BD-1063 at 80 mg/kg also inhibits the development of OIH when Morphine was used.

In the context of the present invention, the following terms have the meaning detailed below.

"Alkyl" refers to a straight or branched hydrocarbon chain radical consisting of 1 to 12 carbon atoms, containing no unsaturation, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkyl radicals have from 1 to 6 carbon atoms. If substituted by aryl, it corresponds to an "Arylalkyl" radical, such as benzyl or phenethyl. If substituted by heterocyclyl, it corresponds to a "Heterocyclylalkyl" radical.

"Alkenyl" refers to a straight or branched hydrocarbon chain radical consisting of 2 to 12 carbon atoms, containing at least one unsaturation, and which is attached to the rest of the molecule by a single bond. Alkenill radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkenyl radicals have from 2 to 6 carbon atoms.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple aromatic ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —$OR_a$ where $R_a$ is an alkyl radical as defined above, e.g., methoxy, ethoxy, propoxy, etc.

"Amino" refers to a radical of the formula —$NH_2$, —$NHR_a$ or —$NR_aR_b$, optionally quaternized, e.g., methylamino, ethylamino, dimethylamino, diethylamino, propylamino, etc.

"Halogen", "halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are preferred particularly, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention— normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a sigma ligand, in particular a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

Any compound referred to herein is intended to represent such specific compound as well as certain variations or forms. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C— or $^{14}$C-enriched carbon, or the replacement of at least one nitrogen by $^{15}$N-enriched nitrogen are within the scope of this invention.

The sigma ligands, in particular the compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient is capable of providing (directly or indirectly) a compound as described herein. However, it will be appreciated that non-pharmaceutically acceptable salts, solvates and prodrugs also fall within the scope of the invention since those may be useful in the preparation of pharmaceutically acceptable salts, solvates and prodrugs. The preparation of salts, solvates and prodrugs can be carried out by methods known in the art.

As used herein, the terms "treat", "treating" and "treatment" include the eradication, removal, reversion, alleviation, modification, or control of opioid-induced hyperalgesia (OIH).

As used herein, the terms "prevention", "preventing", "preventive" "prevent" and prophylaxis refer to the capacity of a therapeutic to avoid, minimize or difficult the onset or development of a disease or condition before its onset, in this case opioid-induced hyperalgesia (OIH).

Therefore, by "treating" or "treatment" and "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as OIH. As such, the method of the present invention also includes situations where the condition is completely inhibited, e.g., prevented from happening, or stopped, e.g., terminated, such that the subject no longer experiences the condition. As such, the present method includes both preventing and managing acute and chronic OIH.

As used herein, the terms "sigma ligand" or "sigma receptor ligand" refer to any compound binding to the sigma receptor. As stated previously, the sigma ligand is preferably a sigma receptor antagonist in the form of a (neutral) antagonist, an inverse agonist or a partial antagonist.

An "agonist" is defined as a compound that binds to a receptor and has an intrinsic effect, and thus, increases the basal activity of a receptor when it contacts the receptor.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist—receptor complex, which, in turn, depends on the nature of antagonist receptor binding.

A "partial antagonist" is defined as a compound that binds to the receptor and generates an antagonist response; however, a partial antagonist does not generate the full antagonist response. Partial antagonists are weak antagonists, thereby blocking partially the action of an agonist or inverse agonist on the receptor.

An "inverse agonist" is defined as a compound that produces an effect opposite to that of the agonist by occupying the same receptor and, thus, decreases the basal activity of a receptor (i.e., signalling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist.

"The sigma receptor/s" as used in this application is/are well known and defined using the following citation: "this binding site represents a typical protein different from opioid, NMDA, dopaminergic, and other known neurotransmitter or hormone receptor families" (G. Ronsisvalle et al. Pure Appl. Chem. 73, 1499-1509 (2001)). Pharmacological data based on ligand binding studies, anatomical distribution and biochemical features distinguish at least two subtypes of σ receptors (R. Quiron et al., Trends Pharmacol. Sci. 13, 85-86 (1992); M. L. Leitner, Eur. J. Pharmacol. 259, 65-69 (1994); S. B. Hellewell and W. D. Bowen; Brain Res. 527, 244-253 (1990)) (G. Ronsisvalle et al. Pure Appl. Chem. 73, 1499-1509 (2001)). The protein sequences of the sigma receptors (Sigma 1 (σ1) and Sigma 2 (σ2)) are known in the art (e.g. Prasad, P. D. et al., J. Neurochem. 70 (2), 443-451 (1998)). They show a very high affinity to various analgesics (e.g. pentazocine).

"Compound/s binding to the sigma receptor" or "sigma ligand" as used in this application is/are defined as a compound having an $IC_{50}$ value of ≤5000 nM, more preferably ≤1000 nM, more preferably ≤500 nM on the sigma receptor. More preferably, the $IC_{50}$ value is ≤250 nM. More preferably, the $IC_{50}$ value is ≤100 nM. Most preferably, the $IC_{50}$ value is ≤50 nM. The half maximal inhibitory concentration (IC50) is a measure of the effectiveness of a compound in inhibiting biological or biochemical function. The IC50 is the concentration of competing ligand which displaces 50% of the specific binding of the radioligand. Additionally, the wording "Compound/s binding to the sigma receptor", as used in the present application is defined as having at least ≥50% displacement using 10 nM radioligand specific for the sigma receptor (e.g. preferably $[^3H]$-(+) pentazocine) whereby the sigma receptor may be any sigma receptor subtype. Preferably, said compounds bind to the sigma-1 receptor subtype.

Compounds binding to the sigma receptor, generally also referred to as sigma ligands, are well known in the art. Many of them are encompassed by the "Compound/s binding to the sigma receptor" definition above. Although there are many known uses for sigma ligands, such as antipsychotic drugs, anxiolytics, antidepressants, stroke treatment, antiepileptic drugs and many other indications, including antimigraine and general pain, there is no mention in the art of these compounds as useful for the treatment of opioid-induced hyperalgesia (OIH) associated to opioid therapy.

Table 1 lists some sigma ligands known in the art (i.e. having an $IC_{50}$≤5000 nM). Some of these compounds may bind to the sigma-1 and/or to the sigma-2 receptor. These sigma ligands also include their respective salts, bases, and acids.

TABLE 1

| | |
|---|---|
| (−)-Cyanopindolol hemifumarate | Cutamesine hydrochloride |
| (−)-(1R,2S)-cis-N-[2-(3,4-Dichlorophenyl)ethyl]-2-pyrrolidinocyclohexylamine | Cyclobenzaprine HCl |
| (−)-1-[1-(3-Chlorophenyl)pyrrolidin-2-ylmethyl]-4-(2-phenylethyl)piperazine | Cycloheximide |
| (−)-Sparteine sulfate pentahydrate | Cyproheptadine HCl |
| (+)-Himbacine | Darrow Red HCl |
| (±)-1-Cyclohexyl-4-[3-(5-methoxy-1,2,3,4-tetrahydronaphthalen-1-yl)propyl]piperazine | Demecarium Bromide |
| (1S,5R)-3-[2-(2-Adamantyl)ethyl]-1,8,8-trimethyl-3-azabicyclo[3.2.1]octane hydrochloride | Denatonium Benzoate |
| (2-Dibutylamino-Ethyl)-Carbamic Acid 2-(4-Benzofuran-2-Ylmethyl-Piperazin-1-Yl)-Ethyl Ester | Deptropine Citrate |
| (4-[1,2,3]Thiadiazol-4-Yl-Benzyl)-Carbamic Acid 1-(3-Methoxy-2-Nitro-Benzyl)-Piperidin-3-Ylmethyl Ester | Desloratadine |
| (4aalpha,8aalpha)-6-(4-Fluorophenyl)-2-(4-pyridylmethyl)-6-hydroxydecahydroisoquinoline; (4a,8a-cis)-6-(4-Fluorophenyl)-2-(pyridin-4-ylmethyl)perhydroisoquinolin-6-ol | Dexbrompheniramine Maleate |
| (4aalpha,8abeta)-2-Benzyl-6-(4-fluorophenyl)-6-hydroxydecahydroisoquinoline | Dexchlorpheniramine Maleate |
| (6aR,9R)-5-Bromo-7-methyl-N-(2-propynyl)-4,6,6a,7,8,9-hexahydroindolo[4,3-fg]quinoline-9-carboxamide | Dexfenfluramine HCl |
| (S)-(−)-N-(2-Amino-3-phenylpropyl)-2-(3,4-dichlorophenyl)-N-methylacetamide hydrochloride | Dicyclomine HCl |
| (S)-Methamphetamine HCl | Diethylpropion HCl |
| [1-(9-Ethyl-9H-Carbazol-3-Ylmethyl)-Pyrrolidin-3-Yl]-Carbamic Acid 1-(3-Benzyloxy-4-Methoxy-Benzyl)-Piperidin-3-Ylmethyl Ester | Dimethisoquin HCl |

TABLE 1-continued

| | |
|---|---|
| [1-(9-Ethyl-9H-Carbazol-3-Ylmethyl)-Pyrrolidin-3-Yl]-Carbamic Acid 2-(Tert-Butoxycarbonyl-Naphthalen-1-Ylmethyl-Amino)-Ethyl Ester | Dimetindene Maleate |
| [4-(4-Ethyl-3,5-Dimethyl-Pyrazol-1-Yl)-Phenyl]-[4-(3-Phenyl-Allyl)-Piperazin-1-Yl]-Methanone | Diphemanil Methylsulfate |
| 1-(1,2-Diphenylethyl)Piperidine Maleate, (+/−) | Diphenidol HCl |
| 1-(1,4-Ethano-1,2,3,4-tetrahydro-2-naphthylmethyl)-4-methylpiperazine hydrate; 1-(Benzobicyclo[2.2.2]octen-2-ylmethyl)-4-methylpiperazine hydrate | Diphenoxylate HCl |
| 1-(1-Adamantyl)-2-[4-(2H-naphtho[1,8-cd]isothiazol-2-ylmethyl)piperidin-1-yl]ethanone S,S-dioxide hydrochloride | Diphenylpyraline HCl |
| 1-(1-Naphthyl)Piperazine HCl | Dipropyldopamine HBr |
| 1-(2-Benzyloxyethyl)-4-(3-phenylpropyl)piperazine dihydrochloride | Doxepin HCl |
| 1-(2-Phenylethyl)piperidine oxalate | Dyclonine HCl |
| 1-(3-Chlorophenyl)Piperazine HCl | Ebastine |
| 1-(3-Chlorothien-2-yl)-2-[4-(4-fluorobenzyl)piperidin-1-yl]ethanol | Econazole Nitrate |
| 1-(4-Bromo-Benzenesulfonyl)-4-(2-Tert-Butylsulfanyl-Benzyl)-Piperazine | Epinastine HCl |
| 1-(4-Chloro-3-hydroxyphenyl)-2-[4-(4-fluorobenzyl)piperidin-1-yl]ethanol | Ethaverine HCl |
| 1-(4-Chlorophenyl)-3-(hexahydroazepin-1-ylmethyl)pyrrolidin-2-one | Ethopropazine HCl |
| 1-(4-Chlorophenyl)-3(R)-[4-(2-methoxyethyl)-1-piperazinylmethyl]pyrrolidin-2-one (−)-D-tartrate | Eticlopride HCl, S(−)- |
| 1-(4-Chlorophenyl)-3(R)-[4-(2-methoxyethyl)piperazin-1-ylmethyl]pyrrolidin-2-one dihydrochloride | Etofenamate |
| 1'-(4-Fluorobenzyl)-1,3-dihydrospiro[2-benzofuran-1,4'-piperidine] | Etonitazenyl Isothiocyanate |
| 1-(4-Fluorophenyl)-4-[4-(5-fluoro-2-pyrimidinyl)-1-piperazinyl]butan-1-ol hydrochloride | Femoxetine HCl |
| 1-(4-Fluorophenyl)-4-[4-(5-fluoropyrimidin-2-yl)piperazin-1-yl]butan-1-ol; 1-[4-(4-Fluorophenyl)-4-hydroxybutyl]-4-(5-fluoropyrimidin-2-yl)piperazine | Fenfluramine HCl |
| 1'-(4-Phenylbutyl)spiro[1,3-dihydroisobenzofuran-1,4'-piperidine] | Fenticonazole Nitrate |
| 1-(Cyclobutylmethyl)-2-[3-phenyl-2(E)-propenyl]pyrrolidine hydrochloride | Fipexide HCl |
| 1-(Cyclohexylmethyl)-3'-methoxy-5'-phenyl-4',5'-dihydro-3'H-spiro[piperidine-4,1'-pyrano[4,3-c]pyrazole] | Flavoxate HCl |
| 1-(Cyclopropylmethyl)-4-[2-(4-fluorophenyl)-2-oxoethyl]piperidine hydrobromide | Flunarizine diHCl |
| 1,4-Bis[spiro[isobenzofuran-1(3H),4'-piperidin]-1'-yl]butane | Fluoxetine Related Compound B |
| 1-[(1R,3R)-2,2-Dimethyl-3-(2-phenoxyethyl)cyclobutylmethyl]piperidine | Fluperlapine |
| 1-[2-(3,4-Dichlorophenyl)ethyl]-3-(pyrrolidin-1-yl)piperidine | Fluphenazine Decanoate DiHCl |
| 1-[2-(3,4-Dichlorophenyl)ethyl]-4-(3-phenylpropyl)piperazine | Fluphenazine Enanthate DiHCl |
| 1-[2-(3,4-Dichlorophenyl)ethyl]-4-methylpiperazine | Fluphenazine HCl |
| 1-[2-(4-Fluorophenyl)ethyl]-4,4-dimethylhexahydroazepine hydrochloride | Fluphenazine N-Mustard DiHCl |
| 1-[2-[1-(3,4-Dichlorophenyl)-5-methyl-1H-1,2,4-triazol-3-ylsulfanyl]ethyl]piperidine oxalate | Flurazepam Related Compound C |
| 1-[2-Benzyloxy-1(R)-phenylethyl]-4-cyclohexylpiperazine dihydrochloride | Fluspirilene |
| 1-[3-(2-Oxo-3-phenylimidazolin-1-yl)propyl]spiro[piperidine-4,1'(3H)-isobenzofuran] hydrochloride; 1-Phenyl-3-[3-[spiro[piperidine-4,1'(3H)-isobenzofuran]-1-yl]propyl]imidazolin-2-one hydrochloride | GBR 12783 DiHCl |
| 1-[3-(3,4-Dimethoxyphenyl)propyl]-4-(4-phenylbutyl)perhydro-1,4-diazepine dihydrochloride | GBR 12909 DiHCl |
| 1-[3-(4-Chlorophenoxy)propyl]-4-methylpiperidine hydrochloride | GBR 13069 DiHCl |

TABLE 1-continued

| | |
|---|---|
| 1-[3-(4-Phenyl-2H-1,2,3-triazol-2-yl)propyl]piperidine | GBR-12935 DiHCl |
| 1-[4-(6-Methoxynaphthalen-1-yl)butyl]-3,3-dimethylpiperidine hydrochloride | GR 89696 Fumarate |
| 1-[4-[2-[1-(3,4-Dichlorophenyl)-1H-pyrazol-3-yloxy]ethyl]piperazin-1-yl]ethanone oxalate | Guanabenz Acetate |
| 11-[5-(4-Fluorophenyl)-5-oxopentyl]-5,6,7,8,9,10-hexahydro-7,10-iminocyclohept[b]indole | Guanadrel Sulfate |
| 1-Benzyl-3beta-[3-(cyclopropylmethoxy)propyl]-2alpha,3alpha,4beta-trimethylpiperidine | Halofantrine HCl |
| 1-Benzyl-3-methoxy-3',4'-dihydrospiro(piperidine-4,1'-thieno[3,2-c]pyrane) | HEAT HCl |
| 1'-Benzyl-3-methoxy-4-phenyl-3,4-dihydrospiro[furo[3,4-c]pyrazole-1,4'-piperidine] | Hexylcaine HCl |
| 1-Benzyl-4-(4-fluorophenoxymethyl)piperidine | Hycanthone |
| 1-Benzyl-4-[2-(4-fluorophenyl)-2-oxoethyl]piperidine maleate | Hydroxychloroquine Sulfate |
| 1-Benzyl-4-[3-phenyl-2(E)-propenyloxymethyl]piperidine hydrochloride | IBZM, S(−)- |
| 1-Benzyl-4-[4-(4-fluorophenyl)-3-cyclohexen-1-yl]piperazine dihydrochloride hemihydrate | ICI-199,441 HCl |
| 1'-Benzylspiro[1,2,3,4-tetrahydronaphthalene-1,4'-piperidine] | Ifenprodil Tartrate |
| 1'-Benzylspiro[indane-1,4'-piperidine] | Indatraline HCl |
| 1'-Butyl-3-Methoxy-4-phenyl-3,4-dihydrospiro[furo[3,4-c]pyrazole-1,4'-piperidine] | Iofetamine HCl |
| 1-Cyclohexyl-4-(3-phenoxypropyl)piperazine dihydrochloride | Isamoltane Hemifumarate |
| 1-Hydroxy-1'-(2-phenylethyl)spiro[1,2,3,4-tetrahydronaphthalene-2,4'-piperidine] hydrochloride | Isoxsuprine HCl |
| 1-Methyl-4-[2-(4-phenylpiperidin-1-yl)ethyl]-4,5,6,7-tetrahydro-1H-indazole oxalate | Ketotifen Fumarate Salt |
| 1-Phenyl-3-(1-propyl-1,2,5,6-tetrahydropyridin-3-yl)-1-propanone oxime oxalate | L-693,403 Maleate |
| 1-Phenyl-4-(pyrrolidin-1-ylmethyl)-1,4,6,7-tetrahydropyrano[4,3-c]pyrazole | L-741,626 |
| 2-(2-{[1-(3-Chloro-Benzyl)-Pyrrolidin-3-Yl]-Methyl-Carbamoyl}-2-Methyl-Propyl)-4,6-Dimethyl-Benzoic Acid | L-741,742 HCl |
| 2-(3,4-Dichlorophenyl)-N-methyl-N-[2-(1,2alpha,3alpha,4beta-tetramethylpiperidin-3beta-yl)ethyl]acetamide | L-745,870 TriHCl |
| 2-(Cyclohexylmethylaminomethyl)-8-methoxy-3,4-dihydro-2H-1-benzopyran hydrochloride | Levetimide HCl, R(−) |
| 2(S)-[(3aS,6aR)-5-Butyl-4-oxo-1,2,3,3a,4,6a-hexahydrocyclopenta[c]pyrrol-2-yl]propionic acid ethyl ester | Levobunolol HCl |
| 2-[2-[5-Methyl-1-(2-naphthyl)-1H-pyrazol-3-yloxy]ethylamino]ethanol hydrochloride | Lidoflazine |
| 2-[2-[N-(Cyclobutylmethyl)-N-methylamino]ethyl]-1,2,3,4-tetrahydronaphthalen-2-one | Lobeline HCl |
| 2-[3-[4-(2-Methoxyphenyl)piperazin-1-yl]propoxy]-9H-carbazole | lomerizine diHCl |
| 2-[4-(4-Methoxybenzyl)piperazin-1-ylmethyl]-4H-1-benzopyran-4-one | Loxapine Succinate |
| 2-[N-[2-(3,4-Dichlorophenyl)ethyl]-N-methylaminomethyl]-1-ethylpyrrolidine | LY-53,857 Maleate |
| 2-Benzyl-3,4,8-trimethyl-2-azabicyclo[2.2.2]octane-6-carboxylic acid ethyl ester | Maprotiline HCl |
| 2-Butyl-2,3,4,4a,9,9a-hexahydro-1H-indeno[2,1-c]pyridine | Mazindol |
| 2-Chloro-11-(4-Methylpiperazino)Dibenz[B,F]Oxepin Maleate | MDL 12,330A HCl |
| 3-(1-Benzyl-2r,3c,4t-trimethylpiperidin-3t-yl)propionic acid ethyl ester hydrochloride | Mebhydroline 1,5-naphthalendisulfonate Salt |
| 3-(3-Chloro-4-cyclohexylphenyl)-1-(hexahydroazepin-1-yl)-1(Z)-propene hydrochloride; 1-[3-(3-Chloro-4-cyclohexylphenyl)-2(Z)-propenyl]hexahydroazepine hydrochloride | Meclizine HCl |

TABLE 1-continued

| | |
|---|---|
| 3-(4-Methylphenyl)-5-(1-propyl-1,2,5,6-tetrahydropyridin-3-yl)isoxazole oxalate | Mefloquine HCl |
| 3-(N-Benzyl-N-methylamino)-1-(4-nitrophenyl)piperidine | Meprylcaine HCl |
| 3,3'-Diethylthiacarbocyanine Iodide | Mesoridazine Besylate |
| 3-[1-(Benzocyclobutan-1-ylmethyl)piperidin-4-yl]-6-fluoro-1,2-benzisoxazole | Metaphit Methanesulfonate |
| 3-[2-(2-Adamantyl)ethyl]-3-azabicyclo[3.2.2]nonane | Metaphit |
| 3-[3-(4-Methylphenyl)isoxazol-5-yl]-1-propyl-1,2,5,6-tetrahydropyridine | Methantheline Bromide |
| 3a,6-Epoxy-2-[2-(4-fluorophenyl)ethyl]-2,3,3a,6,7,7a-hexahydro-1H-isoindole | Methdilazine |
| 3a,6-Epoxy-2-[2-(4-fluorophenyl)ethyl]perhydroisoindole | Methiothepin Mesylate |
| 3-Mercapto-2-Methylpropanoic Acid 1,2-Diphenylethylamine Salt | Methixene HCl |
| 3-Phenyl-1-(1-propyl-1,2,5,6-tetrahydro-3-pyridyl)-1-propanone oxime monohydrochloride | Methylene Violet 3Rax HCl |
| 3-Quinuclidinyl Benzilate | Metipranolol |
| 3-Tropanyl-3,5-Dichlorobenzoate | Mianserin HCl |
| 3-Tropanyl-Indole-3-Carboxylate HCl | Miconazole |
| 4-(1H-Indol-4-Yl)-Piperazine-1-Carboxylic Acid 2-(5-Bromo-2-Ethoxy-Phenylamino)-Cyclohexylmethyl Ester | ML-9 HCl |
| 4-(2-Tert-Butylsulfanyl-Benzyl)-Piperazine-1-Carboxylic Acid 2-Thiophen-2-Yl-Ethyl Ester | Morantel Hydrogen L-Tartrate |
| 4-(3,5-Dimethoxy-Phenyl)-Piperazine-1-Carboxylic Acid 1-(2-Fluoro-Benzyl)-Piperidin-2-Ylmethyl Ester | MR 16728 HCl |
| 4-(3-Nitro-5-Sulfamoyl-Thiophen-2-Yl)-Piperazine-1-Carboxylic Acid 1-(2-Fluoro-5-Methoxy-Benzyl)-Piperidin-3-Ylmethyl Ester | MT-210 |
| 4-(4-Benzylpiperazin-1-ylmethyl)-7-methoxy-2H-1-benzopyran-2-one | N-(2-Adamantyl)-N-[2-(2-adamantyl)ethyl]-N-methylamine hydrochloride |
| 4-(4-Bromophenyl)-5-[2-(dihexylamino)ethyl]thiazol-2-amine dihydrochloride | N-[1-(2-Indanyl)piperidin-4-yl]-N-methylcarbamic acid isobutyl ester fumarate |
| 4-(4-Fluorobenzoyl)-1-(4-Phenylbutyl)Piperidine Oxalate | N-[1-[4-Methoxy-3-(2-phenylethoxy)benzyl]-4-methylpentyl]-N-propylamine |
| 4-(4-Methylphenyl)-1-(3-morpholinopropyl)-1,2,3,6-tetrahydropyridine | N-[2-(3,4-Dichlorophenyl)ethyl]-N-ethyl-N-[2-(1-pyrrolidinyl)ethyl]amine |
| 4-(5-Trifluoromethyl-Pyridin-2-Yl)-Piperazine-1-Carboxylic Acid Pent-2-Ynyl Ester | N-[2-(3,4-Dichlorophenyl)ethyl]-N-methyl-N-(2-pyrrolidinoethyl)amine dihydrobromide |
| 4-(Dimethylamino)-1-phenylcyclohexanol | N-[4-[4-(Diethylamino)piperidin-1-yl]phenyl]methanesulfonamide |
| 4,7-Epoxy-2-[2-(4-fluorophenyl)ethyl]-2,3,3a,4,7,7a-hexahydro-1H-isoindole | N1-(1-Adamantyl)-N2-(2-methylphenyl)acetamidine |
| 4-[1-(3-[18F]fluoropropyl)piperidin-4-ylmethoxy]benzonitrile | N1-[2-(3,4-Dichlorophenyl)ethyl]-N1,N2,N2-trimethyl-1,2-ethanediamine |
| 4-[1-(4-Chlorobenzyl)-4-(benzylpiperidin-4-yl]-2-hydroxy-4-oxobut-2-enoic acid | Nafronyl Oxalate Salt |
| 4-[1-(4-Fluorophenyl)-1-hydroxymethyl]-1-[3-(4-fluorophenoxy)propyl]piperidine | Naftifine |
| 4-[2-(Dipropylamino)ethyl]-2-(2-phenylethoxy)anisole hydrochloride | Naftopidil diHCl |
| 4-[2-(Dipropylamino)ethyl]-5,8-dimethylcarbazole hydrochloride | Naltriben Mesylate |
| 4-[2-[1-(3,4-Dichlorophenyl)-5-methyl-1H-pyrazol-3-yloxy]ethyl]morpholine | NE-100 |
| 4-[2-[1-(Cyclopropylmethyl)piperidin-4-yl]acetyl]benzonitrile fumarate | Nefazodone |
| 4-[4-(N-Benzyl-N-methylamino)piperidin-1-yl]benzonitrile | N-Ethyl-N-[2-(1-piperidinyl)ethyl]-N-[2-[4-(trifluoromethoxy)phenyl]ethyl]amine |
| 4-[N-[2-[N'-(4-Fluorobenzyl)-N'-methylamino]ethyl]-N-methylamino]-1-(4-fluorophenyl)-1-butanone dihydrochloride | Nicergoline |
| 4-Benzyl-1-[4-(4-fluorophenyl)-4-hydroxybutyl]piperidine hydrochloride | Niguldipine HCl, (+/−)- |
| 4-Bromo-N-[1-(9-Ethyl-9H-Carbazol-3-Ylmethyl)-Pyrrolidin-3-Yl]-2-Trifluoromethoxy-Benzenesulfonamide | Nisoxetine HCl |
| 4'-Chloro-3-Alpha-(Diphenylmethoxy)Tropane HCl | NP-07 |
| 4-Furan-2-Ylmethyl-Piperazine-1-Carboxylic Acid 2-{4-[3-(2-Trifluoromethyl-Phenothiazin-10-Yl)-Propyl]-Piperazin-1-Yl}-Ethyl Ester | Nylidrin HCl |
| 4-Methoxy-1-[2-(4-phenylpiperazin-1-yl)ethyl]-6H-dibenzo[b,d]pyran hydrochloride | Octoclothepin Maleate, (±)- |

TABLE 1-continued

| | |
|---|---|
| 4-Methoxy-N-[1-(7-Methoxy-Benzo[1,3]Dioxol-5-Ylmethyl)-Pyrrolidin-3-Yl]-Benzenesulfonamide | Oxamniquine |
| 4-Phenyl-1-(3-phenylpropyl)-4-(pyrrolidin-1-ylcarbonyl)piperidine | Oxamniquine Related Compound A |
| 5-(2-Pyrrolidinoethyl)-4-(2,4,6-trimethoxyphenyl)thiazole-2-amine dihydrochloride | Oxamniquine Related Compound B |
| 5-(N-Ethyl-N-Isopropyl)-Amiloride | Oxatomide |
| 6-[1-Hydroxy-2-[4-(2-phenylethyl)piperidin-1-yl]ethyl]-1,2,3,4-tetrahydroquinolin-2-one | Oxiconazole Nitrate |
| 6-[2-(4-Benzylpiperidin-1-yl)ethyl]-3-methylbenzothiazol-2(3H)-one | Panamesine hydrochloride |
| 6-[2-[4-(2-Phenylethyl)piperidin-1-yl]ethyl]-1,2,3,4-tetrahydroquinolin-2-one | Panaxatriol |
| 6-[3-(Morpholin-4-yl)propyl]benzothiazol-2(3H)-one | PAPP |
| 6-[6-(4-Hydroxypiperidin-1-yl)hexyloxy]-3-methyl-2-phenyl-4H-1-benzopyran-4-one | Paroxetine |
| 7-(4-Methoxyphenyl)-4-[4-(4-pyridyl)butyl]hexahydro-1,4-thiazepine | Paxilline |
| 7-[3-[4-(4-Fluorobenzoyl)piperidin-1-yl]propoxy]-4H-1-benzopyran-4-one hydrochloride | p-Chlorobenzhydrylpiperazine |
| 9-[4-({[4'-(trifluoromethyl)-1,1'-biphenyl-2-yl]carbonyl}amino)piperidin-1-yl]-N-(2,2,2-trifluoroethyl)-9H-fluorene-9-carboxamide | Penbutolol Sulfate |
| 9-Hydroxy-2,3,6,7,7a,8,12b,12c-octahydro-1H,5H-naphtho[1,2,3-ij]quinolizine | Pentamidine Isethionate |
| Acetophenazine Maleate | Pergolide Methanesulfonate |
| Acrinol | Perospirone |
| Ajmaline | Phenamil Methanesulfonate |
| Alaproclate HCl | Phenosafranin HCl |
| Aloe-Emodin | Piboserod |
| Alprenolol D-Tartrate Salt Hydrate | Pimozide |
| Alprenolol HCl | Pinacyanol Chloride |
| AMI-193 | Pindobind, (+/−)- |
| Aminobenztropine | Piperacetazine |
| Amiodarone HCl | Piperidolate HCl |
| Amodiaquine HCl | Pirenperone |
| Amorolfine HCl | PPHT HCl, (±)- |
| Amoxapine | Prenylamine Lactate Salt |
| AN2/AVex-73; AE-37; ANAVEX 2-73; N-(2,2-Diphenyltetrahydrofuran-3-ylmethyl)-N,N-dimethylamine | Pridinol Methanesulfonate Salt |
| Anavex 1-41; AE-14; N-(5,5-Diphenyltetrahydrofuran-3-ylmethyl)-N,N-dimethylamine hydrochloride | Procyclidine HCl |
| Anavex 19-144; AE-37met; AN19/AVex-144 | Proflavine Hemisulfate Salt |
| Anavex 7-1037 | Propafenone HCl |
| Anisotropine Methylbromide | Proparacaine HCl |
| Anpirtoline | Propiomazine |
| ARC 239 DiHCl | Protokylol |
| Auramine O HCl | Protriptyline HCl |
| Azaperone | Pyrilamine Maleate |
| Azatadine Maleate | Pyrimethamine |
| Azelastine HCl | Pyrrolidine-1,2-Dicarboxylic Acid 1-[1-(4-Allyloxy-Benzyl)-Piperidin-2-Ylmethyl] Ester 2-Benzyl Ester |
| Bamethan sulfate | Pyrvinium Pamoate |
| BD 1008 DiHBr | Quetiapine Fumarate |
| BD-1063 | Quinacrine HCl |
| Benextramine TetraHCl | Quinaldine Red |
| Benfluorex HCl | Quipazine Dimaleate |
| Benidipine HCl | Quipazine, 6-Nitro-, Maleate |
| Benoxathian HCl | Raloxifene |
| Benproperine Phosphate | Rimantadine HCl |
| Benzododecinium bromide | Rimcazole hydrochloride |
| Benzphetamine HCl | Risperidone |
| Benztropine Mesylate | Ritanserin |
| Bephenium Hydroxynaphthoate | Ritodrine HCl |
| Bepridil HCl | RS 23597-190 HCl |
| Berberine chloride | RS 67333 HCl |
| Betaxolol HCl | RS 67506 HCl |
| Bifemelane | Safranin O HCl |
| BMY 7378 DiHCl | Salmeterol |
| Bopindolol Malonate | SB203186 |
| BP 554 Maleate | SCH-23390 HCl, R(+)- |
| Bromhexine HCl | Sertaconazole Nitrate |
| Bromodiphenhydramine HCl | Sertindole |

TABLE 1-continued

| | |
|---|---|
| Bromperidol | Sertraline |
| Brompheniramine Maleate | Sibutramine HCl |
| BTCP HCl | Siramesine hydrochloride |
| Buclizine HCl | SKF-525A HCl |
| Buflomedil HCl | SKF-96365 HCl |
| Bupropion HCl | SNC 121 |
| Buspirone HCl | Spiperone HCl |
| Butacaine Sulfate | T-226296 |
| Butaclamol HCl, (±)- | Tegaserod Maleate |
| Butenafine HCl | Terbinafine HCl |
| Butoconazole Nitrate | Terconazole |
| BW 723C86 HCl | Terfenadine |
| Carbetapentane Citrate | Terfenadine Related Compound A |
| Carbinoxamine Maleate | Tetrindole Mesylate |
| Carpipramine DiHCl DiH2O | Thiethylperazine Malate |
| Carvedilol | Thioperamide Maleate |
| Cephapirin Benzathine | Thioproperazine |
| CGS-12066A Maleate | Thioridazine |
| Chloroprocaine HCl | Thiothixene |
| Chlorpheniramine Maleate | Thiothixene, (E)- |
| Chlorphenoxamine HCl | Thonzonium Bromide |
| Chlorprothixene | Tioconazole Related Compound A |
| Cinanserin HCl | TMB-8 HCl |
| Cinnarizine | Tolterodine L-Tartrate |
| Cirazoline HCl | Toremifene Citrate |
| Cis-(+/−)-N-Methyl-N-[2-(3,4-Dichlorophenyl)Ethyl]-2-(1-Pyrrolidinyl)Cyclohexamine DiHBr | Tramazoline HCl |
| Cis(Z)-Flupentixol DiHCl | Trans-U-50488 Methanesulfonate, (±)- |
| cis-2-(Cyclopropylmethyl)-7-(4-fluorobenzoyl)perhydropyrido[1,2-a]pyrazine | Tridihexethyl Chloride |
| cis-2-[4-(Trifluoromethyl)benzyl]-3a,4,7,7a-tetrahydroisoindoline | Trifluoperazine HCl |
| Cisapride Hydrate | Trifluperidol HCl |
| Citalopram HBr | Trihexyphenidyl HCl |
| Clemastine Fumarate | Trimeprazine Hemi-L-Tartrate |
| Clemizole HCl | Trimipramine Maleate |
| Clenbuterol HCl | Tripelennamine HCl |
| Clidinium Bromide | Triprolidine HCl |
| Clobenpropit 2HBr | Triprolidine HCl Z Isomer |
| Clofazimine | Tropanyl 3,5-Dimethylbenzoate |
| Clofilium Tosylate | Tropine 2-(4-Chlorophenoxy)Butanoate, Maleate |
| Clomiphene Citrate | U-50488 HCl, (−)- |
| Clomiphene Related Compound A | U-62066 |
| Clomipramine | UH 232 Maleate, (+)- |
| Cloperastine HCl | Vesamicol HCl |
| Clorgyline HCl | Vinpocetine |
| Clozapine | W-7 HCl |
| Conessine | WB-4101 HCl |

Preferably, the table above includes also reduced haloperidol. Reduced haloperidol is an active metabolite of haloperidol that is produced in humans, shows a high affinity (in the low nanomolar range) for sigma-1 receptors, and produces an irreversible blockade of sigma-1 receptors both in experimental animals and human cells.

Examples of well known methods of producing a prodrug of a given acting compound are known to those skilled in the art (e.g. in Krogsgaard-Larsen et al., Textbook of Drug design and Discovery, Taylor & Francis (April 2002)).

In a preferred embodiment, the sigma ligand in the context of the present invention has the general formula (I) as depicted above.

In a preferred embodiment, $R_1$ in the compounds of formula (I) is selected from H, —$COR_8$, and substituted or unsubstituted alkyl. More preferably, $R_1$ is selected from H, methyl and acetyl. A more preferred embodiment is when $R_1$ is H.

In another preferred embodiment, $R_2$ in the compounds of formula (I) represents H or alkyl, more preferably methyl.

In yet another preferred embodiment of the invention, $R_3$ and $R_4$ in the compounds of formula (I) are situated in the meta and para positions of the phenyl group, and preferably, they are selected independently from halogen and substituted or unsubstituted alkyl.

In an especially preferred embodiment of the invention, in the compounds of formula (I) both $R_3$ and $R_4$ together with the phenyl group form an optionally substituted fused ring system (for example, a substituted or unsubstituted aryl group or a substituted or unsubstituted, aromatic or non-aromatic heterocyclyl group may be fused), more preferably, a naphthyl ring system.

Also in the compounds of formula (I), embodiments where n is selected from 2, 3, 4 are preferred in the context of the present invention, more preferably n is 2.

Finally, in another embodiment it is preferred in the compounds of formula (I) that $R_5$ and $R_6$ are, each independently, $C_{1-6}$ alkyl, or together with the nitrogen atom to which they are attached form a substituted or unsubstituted heterocyclyl group a, in particular a group chosen among morpholinyl, piperidinyl, and pyrrolidinyl group. More preferably, $R_5$ and $R_6$ together form a morpholine-4-yl group.

In preferred variants of the invention, the sigma ligand of formula (I) is selected from:

[1] 4-{2-(1-(3,4-dichlorophenyl)-5-methyl-1H pyrazol-3-yloxy)ethyl}morpholine
[2] 2-[1-(3,4-Dichlorophenyl)-5-methyl-1H-pyrazol-3-yloxy]-N,N-diethylethanamine
[3] 1-(3,4-Dichlorophenyl)-5-methyl-3-[2-(pyrrolidin-1-yl)ethoxy]-1H-pyrazole
[4] 1-(3,4-Dichlorophenyl)-5-methyl-3-[3-(pyrrolidin-1-yl)propoxy]-1H-pyrazole
[5] 1-{2-[1-(3,4-Dichlorophenyl)-5-methyl-1H-pyrazol-3-yloxy]ethyl}piperidine
[6] 1-{2-[1-(3,4-dichlorophenyl)-5-methyl-1H-pyrazol-3-yloxy]ethyl}-1H-imidazole
[7] 3-{1-[2-(1-(3,4-Dichlorophenyl)-5-methyl-1H-pyrazol-3-yloxy)ethyl]piperidin-4-yl}-3H-imidazo[4,5-b]pyridine
[8] 1-{2-[1-(3,4-Dichlorophenyl)-5-methyl-1H-pyrazol-3-yloxy]ethyl}-4-methylpiperazine
[9] Ethyl 4-{2-[1-(3,4-dichlorophenyl)-5-methyl-1H-pyrazol-3-yloxy]ethyl}piperazine carboxylate
[10] 1-(4-(2-(1-(3,4-dichlorophenyl)-5-methyl-1H-pyrazol-3-yloxy)ethyl)piperazin-1-yl)ethanone
[11] 4-{2-[1-(4-Methoxyphenyl)-5-methyl-1H-pyrazol-3-yloxy]ethyl}morpholine
[12] 1-(4-Methoxyphenyl)-5-methyl-3-[2-(pyrrolidin-1-yl)ethoxy]-1H-pyrazole
[13] 1-(4-Methoxyphenyl)-5-methyl-3-[3-(pyrrolidin-1-yl)propoxy]-1H-pyrazole
[14] 1-[2-(1-(4-Methoxyphenyl)-5-methyl-1H-pyrazol-3-yloxy)ethyl]piperidine
[15] 1-{2-[1-(4-Methoxyphenyl)-5-methyl-1H-pyrazol-3-yloxy]ethyl}-1H-imidazole
[16] 4-{2-[1-(3,4-Dichlorophenyl)-5-phenyl-1H-pyrazol-3-yloxy]ethyl}morpholine
[17] 1-(3,4-Dichlorophenyl)-5-phenyl-3-[2-(pyrrolidin-1-yl)ethoxy]-1H-pyrazole
[18] 1-(3,4-Dichlorophenyl)-5-phenyl-3-[3-(pyrrolidin-1-yl)propoxy]-1H-pyrazole
[19] 1-{2-[1-(3,4-Dichlorophenyl)-5-phenyl-1H-pyrazol-3-yloxy]ethyl}piperidine
[20] 1-{2-[1-(3,4-Dichlorophenyl)-5-phenyl-1H-pyrazol-3-yloxy]ethyl}-1H-imidazole
[21] 2-{2-[1-(3,4-dichlorophenyl)-5-phenyl-1H-pyrazol-3-yloxy]ethyl}-1,2,3,4-tetrahydroisoquinoline
[22] 4-{4-[1-(3,4-Dichlorophenyl)-5-methyl-1H-pyrazol-3-yloxy]butyl}morpholine
[23] 1-(3,4-Dichlorophenyl)-5-methyl-3-[4-(pyrrolidin-1-yl)butoxy]-1H-pyrazole
[24] 1-{4-[1-(3,4-Dichlorophenyl)-5-methyl-1H-pyrazol-3-yloxy]butyl}piperidine
[25] 1-{4-[1-(3,4-Dichlorophenyl)-5-methyl-1H-pyrazol-3-yloxy]butyl}-4-methylpiperazine
[26] 1-{4-[1-(3,4-Dichlorophenyl)-5-methyl-1H-pyrazol-3-yloxy]butyl}-1H-imidazole
[27] 4-[1-(3,4-Dichlorophenyl)-5-methyl-1H-pyrazol-3-yloxy]-N,N-diethylbutan-1-amine
[28] 1-{4-[1-(3,4-dichlorophenyl)-5-methyl-1H-pyrazol-3-yloxy]butyl}-4-phenylpiperidine
[29] 1-{4-[1-(3,4-dichlorophenyl)-5-methyl-1H-pyrazol-3-yloxy]butyl}-6,7-dihydro-1H-indol-4(5H)-one
[30] 2-{4-[1-(3,4-dichlorophenyl)-5-methyl-1H-pyrazol-3-yloxy]butyl}-1,2,3,4-tetrahydroisoquinoline
[31] 4-{2-[1-(3,4-dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]-N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-Dichlorophenyl)-5-isopropyl-1H-pyrazol-3-yloxy]ethyl}-1,2,3,4-tetrahydroisoquinoline
[37] 4-{2-[1-(3,4-dichlorophenyl)-1H-pyrazol-3-yloxy]ethyl}morpholine
[38] 2-[1-(3,4-dichlorophenyl)-1H-pyrazol-3-yloxy] N,N-diethylethanamine
[39] 1-(3,4-dichlorophenyl)-3-[2-(pyrrolidin-1-yl)ethoxy]-1H-pyrazole
[40] 1-{2-[1-(3,4-dichlorophenyl)-1H-pyrazol-3-yloxy]ethyl}piperidine
[41] 1-(3,4-dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1-(3,4-Dichlorophenyl)-4,5-dimethyl-1H-pyrazol-3-yloxy]ethyl}morpholine
[45] 4-{2-[1-(3,4-Dichlorophenyl)-4,5-dimethyl-1H-pyrazol-3-yloxy]ethyl}morpholine
[46] 2-[1-(3,4-Dichlorophenyl)-4,5-dimethyl-1H-pyrazol-3-yloxy]-N,N-diethylethanamine
[47] 1-(3,4-Dichlorophenyl)-4,5-dimethyl-3-[2-(pyrrolidin-1-yl)ethoxy]-1H-pyrazole
[48] 1-(3,4-Dichlorophenyl)-4,5-dimethyl-3-[3-(pyrrolidin-1-yl)propoxy]-1H-pyrazole
[49] 1-{2-[1-(3,4-Dichlorophenyl)-4,5-dimethyl-1H-pyrazol-3-yloxy]ethyl}piperidine
[50] 4-{4-[1-(3,4-dichlorophenyl)-1H-pyrazol-3-yloxy]butyl}morpholine
[51] (2S,6R)-4-{4-[1-(3,4-dichlorophenyl)-1H-pyrazol-3-yloxy]butyl}-2,6-dimethylmorpholine
[52] 1-{4-[1-(3,4-Dichlorophenyl)-1H-pyrazol-3-yloxy]butyl}piperidine
[53] 1-(3,4-Dichlorophenyl)-3-[4-(pyrrolidin-1-yl)butoxy]-1H-pyrazole
[55] 4-[1-(3,4-dichlorophenyl)-1H-pyrazol-3-yloxy]-N,N-diethylbutan-1-amine
[56] N-benzyl-4-[1-(3,4-dichlorophenyl)-1H-pyrazol-3-yloxy]-N-methylbutan-1-amine
[57] 4-[1-(3,4-dichlorophenyl)-1H-pyrazol-3-yloxy]-N-(2-methoxyethyl)-N-methylbutan-1-amine
[58] 4-{4-[1-(3,4-dichlorophenyl)-1H-pyrazol-3-yloxy]butyl}thiomorpholine
[59] 1-[1-(3,4-Dichlorophenyl)-5-methyl-3-(2-morpholinoethoxy)-1H-pyrazol-4-yl]ethanone
[60] 1-{1-(3,4-dichlorophenyl)-5-methyl-3-[2-(pyrrolidin-1-yl)ethoxy]-1H-pyrazol-4-yl}ethanone
[61] 1-{1-(3,4-dichlorophenyl)-5-methyl-3-[2-(piperidin-1-yl)ethoxy]-1H-pyrazol-4-yl}ethanone
[62] 1-{1-(3,4-dichlorophenyl)-3-[2-(diethylamino)ethoxy]-5-methyl-1H-pyrazol-4-yl}ethanone
[63] 4-{2-[5-Methyl-1-(naphthalen-2-yl)-1H-pyrazol-3-yloxy]ethyl}morpholine
[64] N,N-Diethyl-2-[5-methyl-1-(naphthalen-2-yl)-1H-pyrazol-3-yloxy]ethanamine
[65] 1-{2-[5-Methyl-1-(naphthalen-2-yl)-1H-pyrazol-3-yloxy]ethyl}piperidine
[66] 5-Methyl-1-(naphthalen-2-yl)-3-[2-(pyrrolidin-1-yl)ethoxy]-1H-pyrazole or their pharmaceutically acceptable salts, isomers, prodrugs or solvates.

In a more preferred variant of the invention, the sigma ligand of formula (I) is 4-{2-[5-Methyl-1-(naphthalen-2-yl)-1H-pyrazol-3-yloxy]ethyl}morpholine. This particular compound is designated in the examples of the present invention as compound 63.

The compounds of formula (I) and their salts or solvates can be prepared as disclosed in the previous application WO2006/021462.

As stated previously, one aspect of this invention refers to the use of sigma ligand as defined above for the manufacture of a medicament for the prevention and/or treatment of OIH associated to opioid therapy.

According to the IASP "hyperalgesia" is defined as "an increased response to a stimulus which is normally painful" (IASP, Classification of chronic pain, $2^{nd}$ Edition, IASP Press (2002), 211).

As noted previously, opioid-induced hyperalgesia or opioid-induced abnormal pain sensitivity is a phenomenon associated with the use of opioids such as morphine, hydrocodone, remifentanyl, oxycodone or methadone. Individuals taking opioids can develop an increasing sensitivity to noxious stimuli, even evolving a painful response to previously non-noxious stimuli (allodynia). Some studies demonstrated that this effect occurs not only after long use of opioids but also after only a single high dose of opioids. Although tolerance and opioid-induced hyperalgesia both result in a similar need for dose escalation, they are nevertheless caused by two distinct mechanisms. The similar net effect makes the two phenomena difficult to distinguish in a clinical setting. Under chronic opioid treatment, a particular individual's requirement for dose escalation may be due to tolerance (desensitization of antinociceptive mechanisms), opioid-induced hyperalgesia (sensitization of pronociceptive mechanisms), or a combination of both. Identifying the development of hyperalgesia is of great clinical importance since patients receiving opioids to relieve pain may paradoxically experience more pain as a result of treatment. Whereas increasing the dose of opioid can be an effective way to overcome tolerance, doing so to compensate for opioid-induced hyperalgesia may worsen the patient's condition by increasing sensitivity to pain while escalating physical dependence. If an individual is taking opioids for a chronic pain condition, and cannot achieve effective pain relief despite increases in dose, they may be experiencing opioid-induced hyperalgesia.

The invention is also directed to a combination of at least one sigma ligand as defined above and at least one opioid or opiate compound for simultaneous, separate or sequential administration, for use in the prevention and/or treatment of opioid-induced hyperalgesia associated to opioid therapy. Compounds that bind to the opioid receptor within the scope of the present invention include natural opiates, such as morphine, codeine and thebaine; semi-synthetic opiates, derived from the natural opioids, such as hydromorphone, hydrocodone, oxycodone, oxymorphone, desomorphine, diacetylmorphine, nicomorphine, dipropanoylmorphine, benzylmorphine and ethylmorphine; fully synthetic opioids, such as fentanyl, pethidine, methadone, tramadol and propoxyphene; and endogenous opioid peptides, produced naturally in the body, such as endorphins, enkephalins, dynorphins, and endomorphins and their analogues. Preferably, the combination according to this invention comprises morphine or its analogues.

The combination of the invention may be formulated for its simultaneous separate or sequential administration, with at least a pharmaceutically acceptable carrier, additive, adjuvant or vehicle. This has the implication that the combination of the two active compounds may be administered:

a) As a combination that is being part of the same medicament formulation, the two active compounds being then administered always simultaneously.

b) As a combination of two units, each with one of the active substances giving rise to the possibility of simultaneous, sequential or separate administration. In a particular embodiment, the sigma ligand is independently administered from the opioid or opiate (i.e in two units) but at the same time. In another particular embodiment, the sigma ligand is administered first, and then the opioid or opiate is separately or sequentially administered. In yet another particular embodiment, the opioid or opiate is administered first, and then the sigma ligand is administered, separately or sequentially, as defined.

The auxiliary materials or additives of a pharmaceutical composition according to the present invention (i.e. a composition comprising at least one sigma ligand or a composition comprising at least one sigma ligand and at least one opioid or opiate compound) can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonar, nasally, rectally and/or intravenously. Therefore, the formulation in accordance with the invention may be adapted for topical or systemic application, particularly for dermal, transdermal, subcutaneous, intramuscular, intra-articular, intraperitoneal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intracisternal, intraspinal, perispinal, intracranial, delivery via needles or catheters with or without pump devices, or other application routes.

Suitable preparations for oral applications are tablets, pills, caplets, gel caps, chewing gums, capsules, granules, drops or syrups.

Suitable preparations for parenteral applications are solutions, suspensions, reconstitutable dry preparations, aerosols or sprays.

The composition of the invention may be formulated as deposits in dissolved form or in patches, for percutaneous application.

Skin applications include ointments, gels, creams, lotions, suspensions or emulsions.

Suitable form of rectal application is by means of suppositories.

Moreover, the composition may be presented in a form suitable for once daily, weekly, or monthly administration.

Accordingly, in another aspect the invention provides a method of treatment of a patient, notably a human, suffering from OIH associated to opioid therapy, which comprises administering to the patient in need of such a treatment or prophylaxis a therapeutically effective amount of a sigma ligand as defined above.

In certain embodiments, hyperalgesia is suppressed, ameliorated and/or prevented. In certain embodiments, the sigma ligand can be administered prior to an activity likely to result in hyperalgelsia, i.e. opioid administration. For example, the formulation can be administered 30 minutes, 1 hour, 2 hours, 5 hours, 10 hours, 15 hours, 24 hours or even more, such as 1 day, several days, or even a week, two weeks, three weeks, or more prior to the activity likely to result in hyperalgelsia, i.e. prior to opioid administration. In other embodiments, the sigma ligand can be administered during and/or after the administration of the opioid. In some instances, the sigma ligand is administered 1 hour, 2 hours, 3 hours, 4 hours, 6 hours, 8 hours, 12 hours, 24 hours, 30 hours, 36 hours, or more, after the administration of the opioid.

In one embodiment of the invention it is preferred that the sigma ligand is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of condition being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

For example, the dosage regime that must be administered to the patient will depend on the patient's weight, the type of application, the condition and severity of the disease. A preferred dosage regime of comprises an administration of a compound according the present invention within a range of 0.01 to 300 mg/kg, more preferably 0.01 to 100 mg/kg, and most preferable 0.01 to 50 mg/kg.

The following examples are merely illustrative of certain embodiments of the invention and cannot be considered as restricting it in any way.

EXAMPLES

Example 1

Synthesis of 4-{2-[5-Methyl-1-(naphthalen-2-yl)-1H-pyrazol-3-yloxy]ethyl}morpholine (compound 63) and its hydrochloride salt

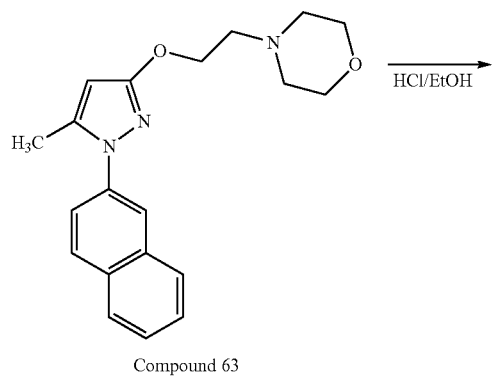

Compound 63

-continued

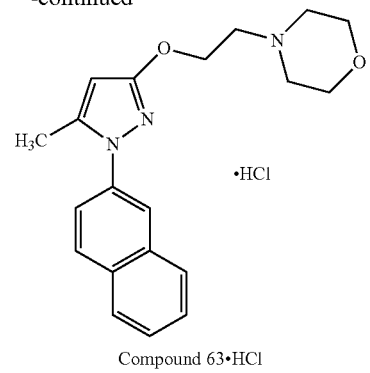

Compound 63·HCl

Compound 63 can be can be prepared as disclosed in the previous application WO2006/021462. Its hydrochloride can be obtained according the following procedure:

Compound 63 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.).

$^1$H-NMR (DMSO-$d_6$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%.

Example 2

Modulation on Mechanical Sensitization Induced by Opioid Administration in Operated (Plantar Incision) and Naïve Rats: Effect of Sigma Antagonists Plantar Incision Surgery The incisional pain model was adapted from Brennan et al. (1996). The induction of anaesthesia in rats was performed with 3% isofluoran for veterinary use, employing an Ohmeda vaporizer and an anaesthesia chamber. Anaesthesia was kept during the surgical operation by a tube which directs the isofluran vapours to the animal's snout. Once the rats were anaesthetised, they were laid down in a prone position and their right hindpaws were cleaned out with alcohol.

Then, a skin incision in the hind paw of about 10 mm was made by means of a scalpel, starting about 5 mm from the heel and extending toward the toes. Fascia was located and by means of curve scissors muscle was elevated and a longitudinal incision of about 5 mm was made, thus the muscle origin and insertion remained intact. Therefore, both superficial (skin) and deep (muscle) tissues and nerves were injured. The skin of the paw was stitched with a suturing stitch with breaded silk (3.0) and the wound was cleaned out with iodinated povidone.

Behavioural Test

Mechanical allodynia was tested using von Frey filaments: Animals were placed in methacrylate cylinders on an elevated surface, with metallic mesh floor perforated in order to apply the filaments. After an acclimation period of about 30 minutes within the cylinders, both hindpaws were stimulated (the injured and the non-injured paw, serving the latter as control), starting with the lowest force filament (0.4 g) and reaching a 15 g filament. The animal's response to pain was manifested by the withdrawal of the paw as a consequence of the painful stimulus caused by a filament. The pressure (force in grams) threshold eliciting the withdrawal of the paw was recorded.

Experimental Protocol 1: Coadministration Studies in Operated Rats

The effect of opioids (morphine, remifentanil, fentanyl or sufentanil) and sigma antagonists (compound 63 or BD-1063) in operated rats were evaluated in a co-treatment paradigm as follows: the opioid drug is administrated through the intraperitoneal route in three consecutive administrations: at the time of surgery, 15 minutes later and 30 minutes after surgery. The sigma antagonist is administrated only once either 30 minutes before surgery (paradigm 1) or 30 minutes after surgery (paradigm 2). FIG. 1 is a schematic representation showing the time course for the two paradigms followed in experimental protocol n° 1.

The doses of remifentanil per administration were 0.066 mg/kg each time (0.2 mg/kg total). The doses of morphine were 3.3 mg/kg each time (10 mg/kg in total). The doses of fentanyl per administration were 0.16 mg/kg each time (0.48 mg/kg total). The doses of sufentanil per administration were 0.05 mg/kg each time (0.15 mg/kg total). The doses used for the single administration of sigma antagonist (BD-1063 and compound 63) were 20, 40 and 80 mg/kg.

Assessment of mechanical allodynia was done 4, 24, 48, 72 and 96 hours after surgery. Additional evaluations were performed on days 5, 6, 7 and 8 after surgery when coadministration of compound 63 and opioids were assessed. The results are shown in FIGS. 2-5 and 10-11.

As expected, the plantar incision surgery produced a significant decrease of the mechanical sensitization threshold as measured with the von Frey filaments application (tactile allodynia for 2 days; FIGS. 2-5) in control rats (vehicle group) that almost recovered their normal threshold at day 3-4. Opioid administration (remiphentanyl in FIGS. 2 and 3; morphine in FIGS. 4 and 5; fentanyl in FIG. 10; sufentanil in FIG. 11) initially induced an analgesic effect 4 hours after operation. However, the analgesic effect disappeared 24 hours later and consecutive daily measurements of paw withdrawal showed an enhancement of tactile allodynia (that is OIH) respect to vehicle treatment that is evidenciable from day 3 to day 6-7.

Administration of 20 mg/kg of compound n° 63 during the perioperative period on day 0 strongly reduced the enhancement of allodynia induced by perioperative remiphentanyl (FIGS. 2 and 3), morphine (FIG. 4), fentanyl (FIG. 10) and sufentanil (FIG. 11) administration. Furthermore, 40 and 80 mg/kg of compound n° 63 also inhibit dose-dependently the decrease of the mechanical sensitization threshold induced by the surgery.

Administration of 80 mg/kg of BD-1063 during the perioperative period on day 0 strongly reduced the enhancement of allodynia induced by perioperative morphine (FIG. 5) administration.

Altogether, data obtained following this experimental approach (perioperative co-administration of sigma ligands and opioids) indicate that sigma ligands are able to prevent the development of OIH.

Experimental Protocol 2: OIH Precipitated by Naloxone

In the previous study (experimental protocol 1), it has been shown that the perioperative administration of morphine, fentanyl, sufentanil or remifentanil enhances the extent and duration of postoperative pain (hyperalgesia). In contrast, the co-administration of compound n° 63 inhibits dose-dependently the development of OIH. To further study the effect on OIH, the mechanical threshold in these opioid-treated rats was evaluated by administering naloxone since naloxone-precipitated opioid abstinence is associated with an enhancement of reflex responses to noxious stimulation (hyperalgesia).

Figure 12:
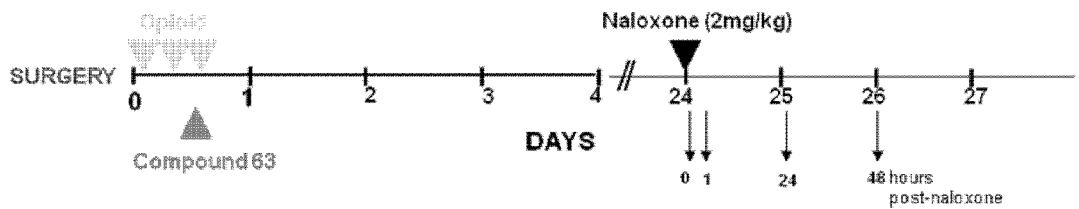
FIG. 12: Schematic representation of experimental protocol n° 2 (OIH precipitated by naloxone).
Figure 13:
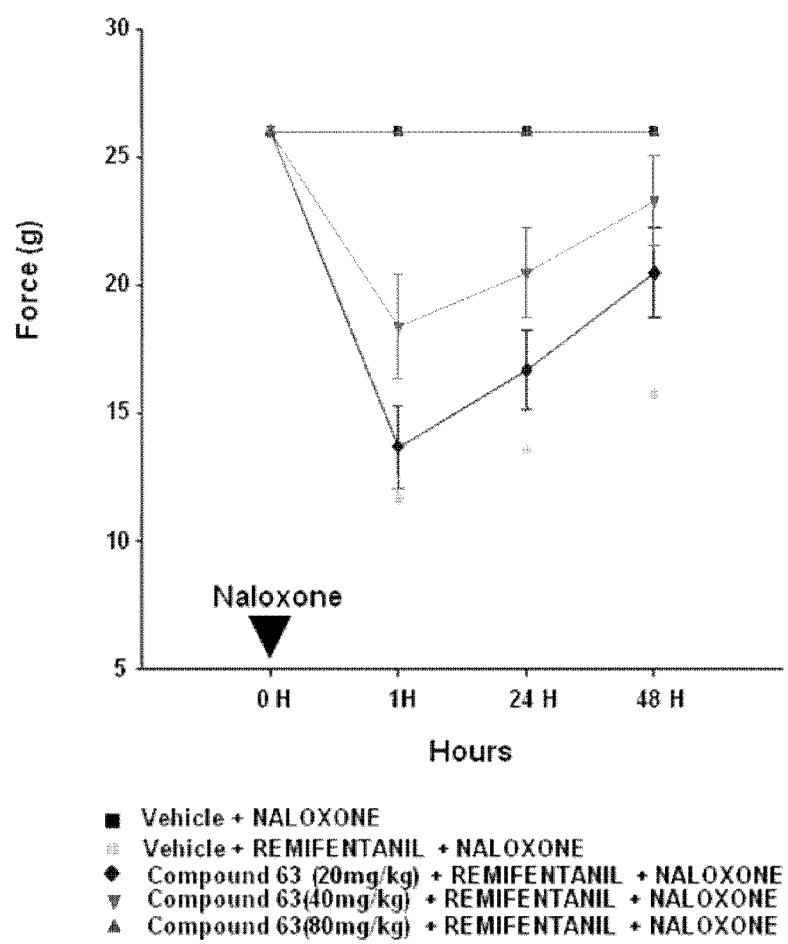
FIG. 13: It shows the effect of Remifentanil (opioid receptor agonist) and compound n° 63 (sigma antagonist) according to experimental protocol n° 2 (OIH precipitated by naloxone).
Figure 14:
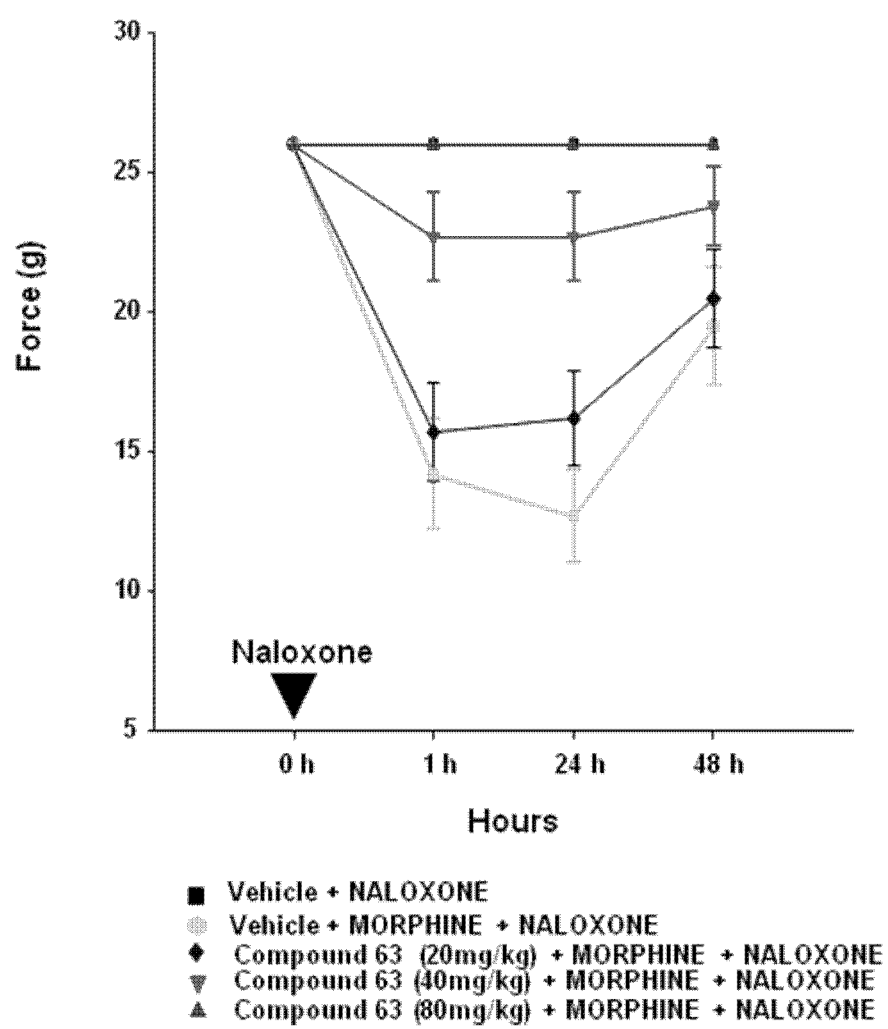
FIG. 14: It shows the effect of Morphine (opioid receptor agonist) and compound n° 63 (sigma antagonist) according to experimental protocol n° 2 (OIH precipitated by naloxone).
Figure 15:
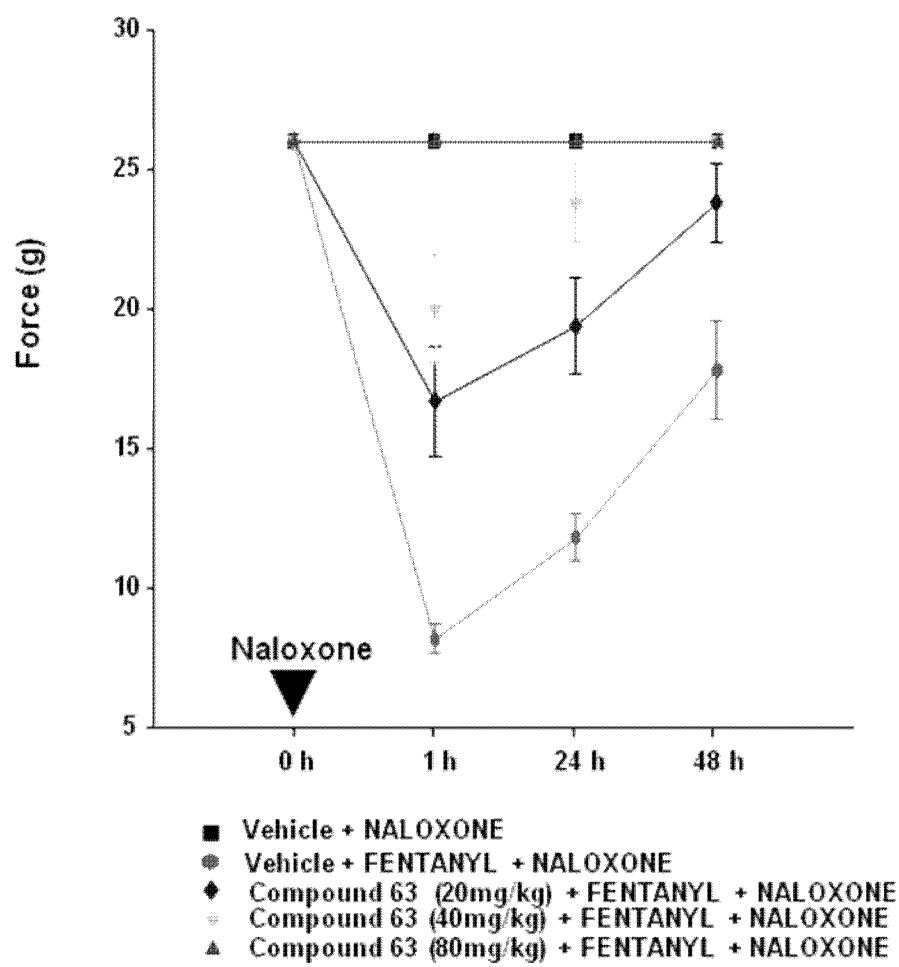
FIG. 15: It shows the effect of Fentanyl (opioid receptor agonist) and compound n° 63 (sigma antagonist) according to experimental protocol n° 2 (OIH precipitated by naloxone).
Figure 16:
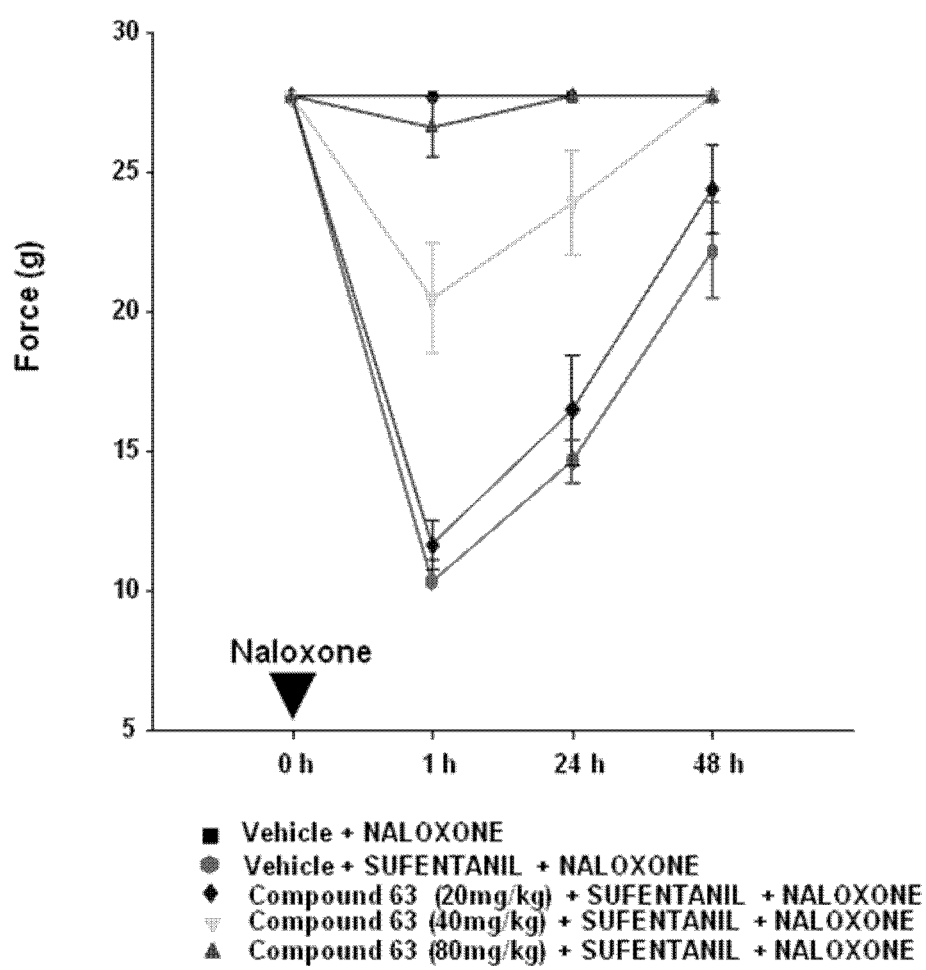
FIG. 16: It shows the effect of Sufentanil (opioid receptor agonist) and compound n° 63 (sigma antagonist) according to experimental protocol n° 2 (OIH precipitated by naloxone).

Thus, when rats had recovered their pre-drug nociceptive threshold value after the opioid or co-administration treatment (21 days later), the ability of naloxone to precipitate hyperalgesia in rats was tested by measuring the withdrawal responses using the von Frey filaments. FIG. 12 is a schematic representation showing the time course for experimental protocol n° 2.

The long lasting effects of morphine, remifentanil, fentanyl and sufentanil, and the effects of compound n° 63 co-administration on pharmacological effects of the opioids were studied following this protocol. In particular, the treatment schedule was as follows: morphine (3.3 mg/kg), remifentanil (0.2 mg/kg), fentanyl (0.16 mg/kg), sufentanil (0.05 mg/kg) or vehicle was injected three times every 15 min starting at the time of plantar incision. The single injection of compound n° 63 was co-administered with the last dose of opioid. At the end of these experiments, on day 21, all rats received a naloxone injection (2 mg/kg), and the nociceptive threshold was measured 1, 24 and 48 hours later (see FIGS. 13-16).

As shown above in experimental protocol 1, the nociceptive threshold was returned to basal 10 days after opioids administrations. The injection of naloxone on day 21 (11 days after the animals had completely recovered their pre-drug nociceptive threshold value) induced a significant decrease in the nociceptive threshold below the basal value. On the other hand, no significant effect of naloxone was observed in vehicle saline-treated rats. Moreover, naloxone was also unable to precipitate hyperalgesia when it was injected on day 21 in opioid-treated rats that had been co-administrated with 80 mg/kg of compound n° 63 (20 and 40 mg/kg produced an attenuation of naloxone-precipitated hyperalgesia) (see FIGS. 13-16).

Experimental Protocol 3: Coadministration Studies in Naïve Rats.

Figure 6:
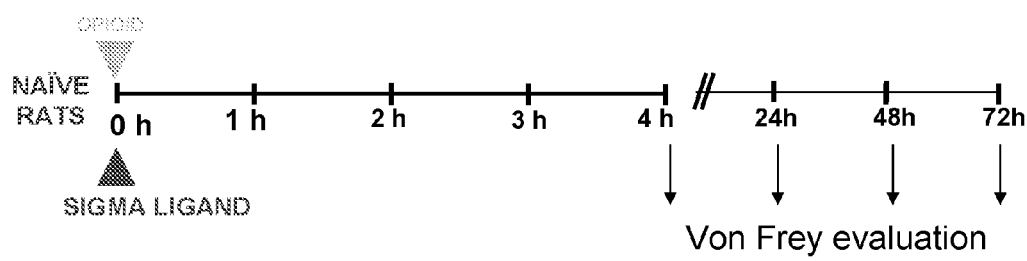
FIG. 6: Schematic representation of experimental protocol n° 3 (co-administration studies in naïve rats) showing the time course for the assessment of Mechanical Sensitization (i.e., OIH) induced by opioids.

The effect of opioids (morphine or remiphentanyl) and sigma antagonists (compound 63 or BD-1063) in naïve rats was evaluated in a co-treatment paradigm by intraperitoneal administration at the same time (FIG. 6).

Naïve rats were administrated with 0.3 mg/kg of remifentanil or 10 mg/kg of morphine. The doses of BD-1063 or compound n° 63 were 20, 40 and 80 mg/kg.

Figure 8:
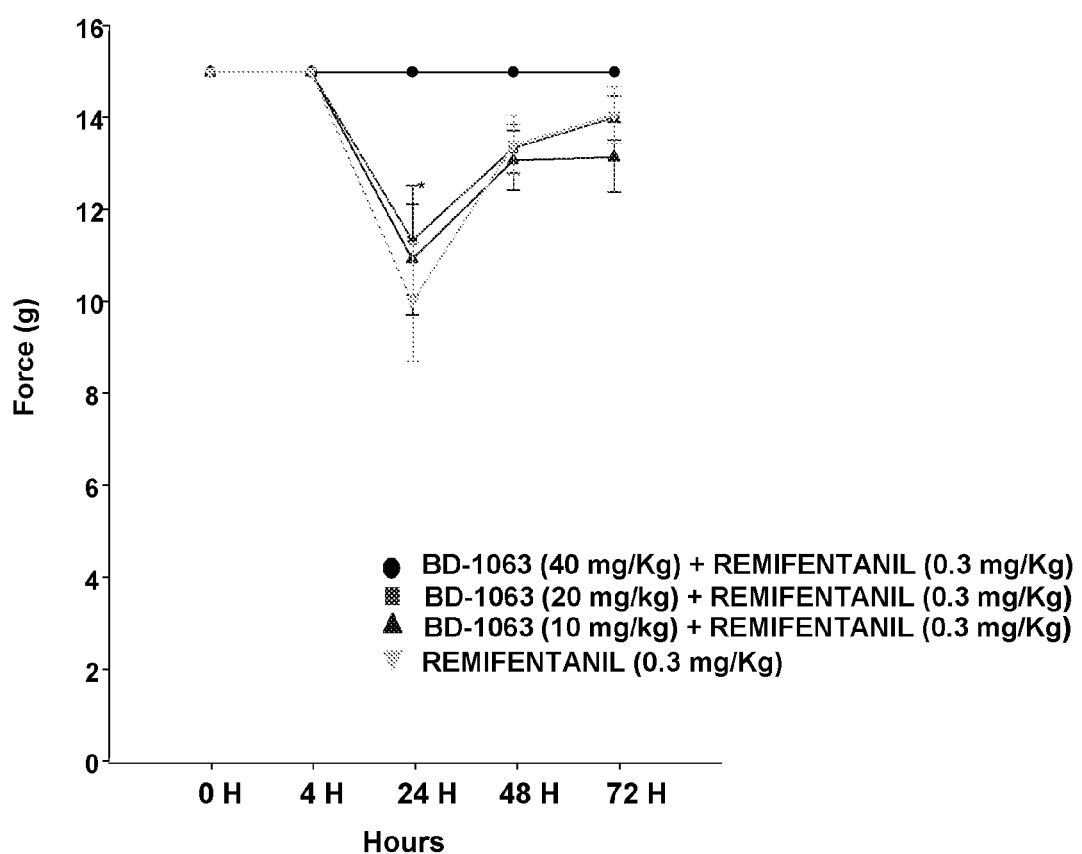
FIG. 8: It shows the effect of Remifentanil (opioid ligand) and compound BD-1063 (sigma antagonist) according to experimental protocol n° 3 (co-administration studies in naïve rats). Similar to compound n° 63, BD-1063 is able to inhibit OIH (i.e., remifentanil-induced hyperalgesia) when administered at 40 mg/kg.
Figure 9:
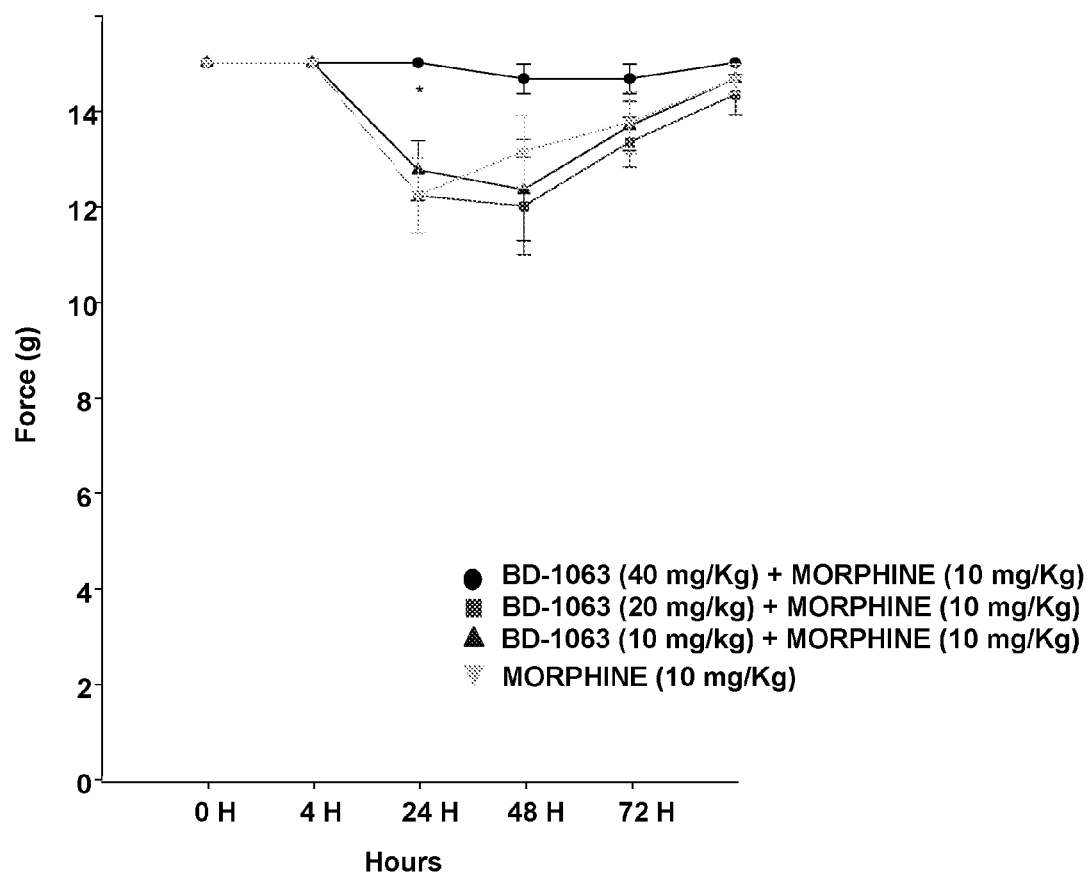
FIG. 9: It shows the effect of Morphine (opioid ligand) and compound BD-1063 (sigma antagonist) according to experimental protocol n° 3 (co-administration studies in naïve rats). Not only remifentanil- but also morphine-induced hyperalgesia is inhibited by the sigma ligand BD-1063 when co-administered to naïve rats at 40 mg/kg together with the opioid.
Figure 10:
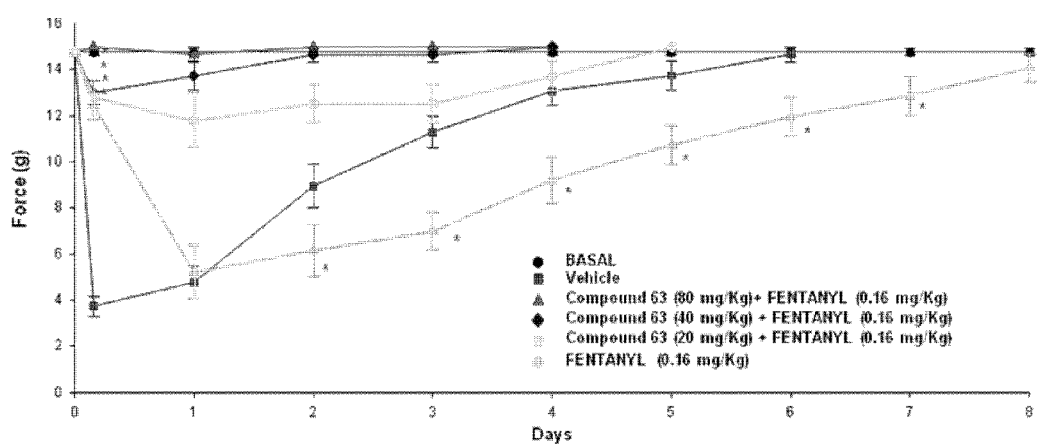
FIG. 10: It shows the effect of Fentanyl (opioid receptor agonist) and compound n° 63 (sigma antagonist) approached by Paradigm 2 according to experimental protocol n° 1 (co-administration studies in the perioperative period).
Figure 11:
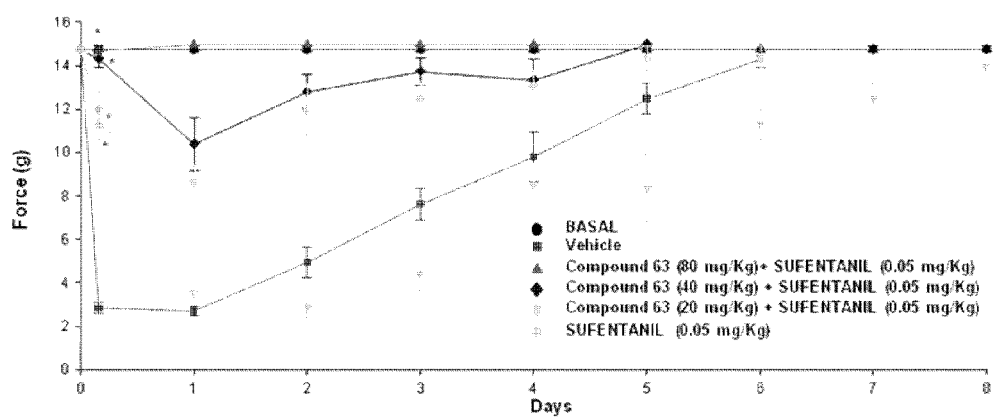
FIG. 11: It shows the effect of Sufentanil (opioid receptor agonist) and compound n° 63 (sigma antagonist) approached by Paradigm 2 according to experimental protocol n° 1 (co-administration studies in the perioperative period).

Assessment of mechanical allodynia was done 4, 24, 48 and 72 hours after surgery. The results are shown in FIGS. 7-9.

Opioid administration to naïve rats produces, 24 hours after, a significant decrease of the mechanical threshold (that is OIH) as measured with the von Frey filaments application (tactile allodynia for 2 days; FIGS. 7-9). Three days later rats recovered their normal threshold.

Figure 7:
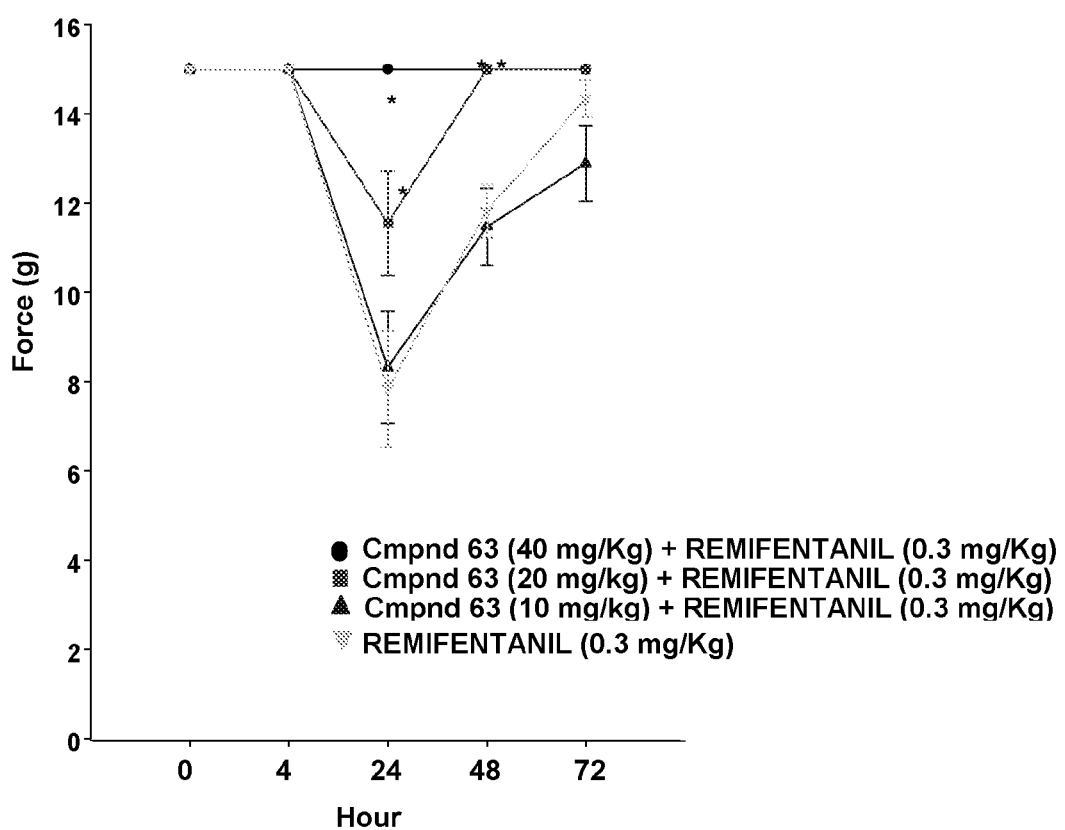
FIG. 7: It shows the effect of Remifentanil (opioid ligand) and compound n° 63 (sigma antagonist) according to experimental protocol n° 3 (co-administration studies in naïve rats). The FIG. 7 shows the inhibitory effect of compound n° 63 on remifentanil-induced hyperalgesia. The inhibitory effect on OIH is clear at 20 and 40 mg/kg.

Compound n° 63 coadministration reduces dose-dependently the enhancement of allodynia induced by remifentanil administration (FIG. 7).

BD-1063 coadministration also reduces the enhancement of allodynia induced by remifentanil (FIG. 8) and morphine (FIG. 9) administration.

Altogether, data obtained following this experimental approach (co-administration of sigma ligands and opioids to naïve rats) indicate that opioids induce OIH, evidenciable from day 1-2 after opioid administration, and that the co-administration of sigma ligands prevents the development of OIH.

The invention claimed is:

1. A method of treatment and/or prophylaxis of opioid-induced hyperalgesia (OIH) associated with opioid therapy in a patient, the method comprising:
   (a) providing a patient who is suffering from OIH associated with opioid therapy, undergoing opioid therapy, or about to undergo opioid therapy, wherein the patient who is undergoing opioid therapy or is about to undergo opioid therapy is or will be receiving a dose of opioid that would be expected to induce OIH in the patient; and
   (b) administering to the patient a therapeutically effective amount of a sigma ligand, wherein the sigma ligand is 4-{2-[5-methyl-1-(naphthalen-2-yl)-1H-pyrazol-3-yloxy]ethyl} morpholine:
      or a pharmaceutically acceptable salt or solvate thereof,
   whereby OIH in the patient is treated, prevented, or ameliorated.

2. The method of claim 1, wherein the sigma ligand is 4-{2-[5-methyl-1-(naphthalen-2-yl)-1H-pyrazol-3-yloxy]ethyl} morpholine hydrochloride.

3. A method of treatment and/or prophylaxis of opioid-induced hyperalgesia (OIH) associated with opioid therapy in a patient, the method comprising:
   (a) providing a patient who is suffering from OIH associated with opioid therapy, undergoing opioid therapy, or about to undergo opioid therapy, wherein the patient who is undergoing opioid therapy or is about to undergo opioid therapy is or will be receiving a dose of opioid that would be expected to induce OIH in the patient; and
   (b) administering to the patient a therapeutically effective amount of a combination of at least one sigma ligand and at least one opioid or opiate compound, wherein said at least one sigma ligand and at least one opioid or compound are administered simultaneously, separately, or sequentially to the patient,
   wherein the sigma ligand is 4-{2-[5-methyl-1-(naphthalen-2-yl)-1H-pyrazol-3-yloxy]ethyl} morpholine:
      or a pharmaceutically acceptable salt or solvate thereof,
   whereby OIH in the patient is treated, prevented, or ameliorated.

4. The method of claim 1, wherein the opioid therapy is selected from the group consisting of morphine therapy, remifentanil therapy, fentanyl therapy, and sufentanil therapy.

5. The method of claim 3, wherein the sigma ligand is 4-{2-[5-methyl-1-(naphthalen-2-yl)-1H-pyrazol-3-yloxy]ethyl} morpholine hydrochloride.

6. The method of claim 3, wherein the opioid therapy is selected from the group consisting of morphine therapy, remifentanil therapy, fentanyl therapy, and sufentanil therapy.

* * * * *